(12) United States Patent
Mattila et al.

(10) Patent No.: US 12,383,181 B2
(45) Date of Patent: Aug. 12, 2025

(54) ELASTIC WEARABLE SENSOR

(71) Applicant: Otsuka Pharmaceutical Co., Ltd., Tokyo (JP)

(72) Inventors: Tomi Mattila, Espoo (FI); Kimmo Jokelainen, Ii (FI); Samuli Yrjänä, Oulu (FI); Colm McCaffrey, Helsinki (FI); Mohammadhossein Behfar, Espoo (FI); Jukka Kyynäräinen, Espoo (FI); Arto Rantala, Espoo (FI)

(73) Assignee: OTSUKA PHARMACEUTICAL CO, LTD., Tokyo (JP)

( * ) Notice: Subject to any disclaimer, the term of this patent is extended or adjusted under 35 U.S.C. 154(b) by 743 days.

(21) Appl. No.: 17/424,757

(22) PCT Filed: Jan. 24, 2020

(86) PCT No.: PCT/JP2020/002521
§ 371 (c)(1),
(2) Date: Jul. 21, 2021

(87) PCT Pub. No.: WO2020/153479
PCT Pub. Date: Jul. 30, 2020

(65) Prior Publication Data
US 2022/0133200 A1 May 5, 2022

Related U.S. Application Data

(60) Provisional application No. 62/796,435, filed on Jan. 24, 2019.

(51) Int. Cl.
*A61B 5/257* (2021.01)
(52) U.S. Cl.
CPC .................................. *A61B 5/257* (2021.01)

(58) Field of Classification Search
CPC .. A61B 5/257; A61B 5/25; A61B 5/24; A61B 5/251
See application file for complete search history.

(56) References Cited

U.S. PATENT DOCUMENTS

| | | | |
|---|---|---|---|
| 4,957,109 | A | 9/1990 | Groeger et al. |
| 6,129,929 | A | 10/2000 | Wick |

(Continued)

FOREIGN PATENT DOCUMENTS

| | | | |
|---|---|---|---|
| CN | 101385645 | A | 3/2009 |
| CN | 104144638 | A | 11/2014 |

(Continued)

OTHER PUBLICATIONS

Translation of DE-202013011290-U1, 2014 (Year: 2014).*

(Continued)

*Primary Examiner* — Adam Z Minchella
(74) *Attorney, Agent, or Firm* — Pillsbury Winthrop Shaw Pittman LLP

(57) ABSTRACT

In some embodiments, a system includes a first assembly, a second assembly, and a connecting member. The first assembly includes a first electrode and a first adhesive portion. The first assembly is configured to be coupled to a surface of a patient via the first adhesive portion. The second assembly includes a second electrode and a second adhesive portion. The second assembly is configured to be coupled to the surface of the patient via the second adhesive portion. The connecting member has a first end coupled to the first assembly and a second end coupled to the second assembly. The connecting member is configured to transition between a first configuration and a second configuration and may be configured to be coupled to the surface of the patient via a third adhesive portion in both the first configuration and the second configuration.

14 Claims, 14 Drawing Sheets

(56) References Cited

U.S. PATENT DOCUMENTS

| | | | |
|---|---|---|---|
| 6,278,036 | B1 | 8/2001 | Anhauser et al. |
| 6,572,636 | B1 | 6/2003 | Hagen et al. |
| 8,688,189 | B2 | 4/2014 | Shennib |
| 8,897,868 | B2 | 11/2014 | Mazar et al. |
| 11,095,821 | B2 | 8/2021 | Katayama |
| 2006/0030781 | A1 | 2/2006 | Shennib |
| 2006/0030782 | A1 | 2/2006 | Shennib |
| 2006/0224072 | A1 | 10/2006 | Shennib |
| 2007/0260133 | A1 | 11/2007 | Meyer |
| 2007/0299471 | A1 | 12/2007 | Takahashi et al. |
| 2008/0135408 | A1* | 6/2008 | Sjolander ............. A61B 5/1468 204/403.01 |
| 2009/0076365 | A1 | 3/2009 | Grassl |
| 2009/0264792 | A1 | 10/2009 | Mazar |
| 2011/0009729 | A1* | 1/2011 | Shin .................. A61B 5/6833 600/391 |
| 2011/0130640 | A1* | 6/2011 | Dunagan ............. A61B 5/6804 600/388 |
| 2011/0160601 | A1 | 6/2011 | Wang et al. |
| 2015/0018643 | A1 | 1/2015 | Cole et al. |
| 2016/0135746 | A1 | 5/2016 | Kumar et al. |
| 2016/0166170 | A1 | 6/2016 | Quintanar et al. |
| 2016/0262649 | A1* | 9/2016 | Hayes-Gill ............ A61B 5/339 |
| 2017/0265770 | A1 | 9/2017 | Quinlan |
| 2018/0014783 | A1 | 1/2018 | Shi et al. |
| 2019/0000341 | A1 | 1/2019 | Xu et al. |
| 2022/0117533 | A1 | 4/2022 | Mattila et al. |
| 2022/0117534 | A1 | 4/2022 | Mattila et al. |

FOREIGN PATENT DOCUMENTS

| | | | |
|---|---|---|---|
| CN | 105050495 | A | 11/2015 |
| CN | 102112572 | | 4/2017 |
| CN | 106923816 | A | 7/2017 |
| DE | 202013011290 | U1 * | 4/2014 ............. A61B 5/282 |
| EP | 0356614 | A2 | 3/1990 |
| EP | 0 509 689 | A2 | 10/1992 |
| EP | 0596604 | A1 | 5/1994 |
| EP | 0882460 | A2 | 12/1998 |
| EP | 1104325 | A1 | 6/2001 |
| EP | 2105089 | A1 | 9/2009 |
| EP | 2854937 | A1 | 4/2015 |
| EP | 3348490 | A1 | 7/2018 |
| GB | 2540955 | A | 2/2017 |
| JP | 4261699 | B2 | 4/2009 |
| JP | 5442112 | B2 | 3/2014 |
| JP | 5693874 | B2 | 4/2015 |
| TW | 201501692 | A | 1/2015 |
| TW | 201825045 | A | 7/2018 |
| WO | WO-2010017276 | A2 | 2/2010 |
| WO | WO-2013059600 | A1 | 4/2013 |
| WO | WO-2013121415 | A1 | 8/2013 |
| WO | 2014/116816 | A1 | 7/2014 |
| WO | 2014/151925 | A1 | 9/2014 |
| WO | WO-2015055289 | A2 | 4/2015 |
| WO | 2016/053731 | A1 | 4/2016 |
| WO | WO-2016052818 | A1 | 4/2016 |
| WO | WO-2017184596 | A1 | 10/2017 |
| WO | 2018/098417 | A1 | 5/2018 |
| WO | WO-2020153479 | A2 | 7/2020 |
| WO | WO-2020179922 | A1 | 9/2020 |
| WO | WO-2020179924 | A1 | 9/2020 |

OTHER PUBLICATIONS

Translation of DE 202013011290 (Year: 2013).*
International Preliminary Report on Patentability for International Application No. PCT/JP2020/002521, mailed Aug. 5, 2021, 16 pages.
International Search Report for International Application No. PCT/JP2020/002521, mailed Jul. 28, 2020, 6 pages.
AliveCor, Inc. "KardiaBand System Instructions for Use," (Nov. 2017), 2 pages.
AliveCor, Inc., "Kardia Mobile Instructions for Use," (Nov. 2016), 2 pages.
Altini, M., "On Heart Rate Variability and the Apple Watch," (Nov. 10, 2018), 15 pages.
Cardiac Insight, Inc., "Cardeo Solo Operator's Manual," Model S300, (Dec. 2018), 65 pages.
CardioComm Solutions, Inc., Press Release, "CardioComm Solutions Introduces the HeartCheckTM ECG Sport—A Smartphone Connected, Wearable, Single & Multi-lead ECG Chest Patch," [online], Retrieved from the Internet: https://www.cardiocommsolutions.com/news/2016/CCSnews_102016.html, (Oct. 20, 2016), 4 pages.
HeartCheck Handheld ECG Monitor Instruction Manual MD100B, Edition: VER1.0B1, Jul. 20, 2010, 35 pages.
International Preliminary Report on Patentability for International Application No. PCT/JP2020/009803 mailed Jun. 11, 2021, 7 pages.
International Preliminary Report on Patentability for International Application No. PCT/JP2020/009815 mailed Apr. 12, 2021, 10 pages.
International Search Report and Written Opinion of the International Searching Authority for International Application No. PCT/JP2020/009803 mailed May 28, 2020, 12 pages.
International Search Report and Written Opinion of the International Searching Authority for International Application No. PCT/JP2020/009815 mailed May 28, 2020, 14 pages.
IRhythm Technologies, Inc., ZioXT Patch Patient Experience Brochure, Feb. 2016, 12 pages.
Lindsey, D. P. et al., "A New Technique for Transmission of Signals from Implantable Transducers," IEEE Transactions on Biomedical Engineering, vol. 45, No. 5, pp. 614-619 (May 1998).
"Maxim Integrated Launches a Movesense Based ECG Development Platform," [online], Retrieved from the Internet: https://www.movesense.com/news/2018/06/maxim-integrated-launches-a-movesense-based-ecg-development-platform/, (Jun. 25, 2018), 4 pages.
MC10 BioStamp nPoint User Manual, Copyright 2016, 72 pages.
MC10, "Introducing BioStamp nPoint, Making Virtual Clinical Trials a Reality," [online], Retrieved from the Internet: https://web.archive.org/web/20181217224816/https:/www.mc10inc.com/, (Dec. 17, 2018), 8 pages.
Medqor, "Actiwave Cardio by CamNTech," [online], Retrieved from the Internet: https://sleepreviewmag.com/sleep-diagnostics/in-lab-tests/polysomnography/actiwave-cardio-by-camntech/, (Nov. 25, 2013), 3 pages.
Medtronic, SEEQ Mobile Cardiac Telemetry (MCT) System, Instructions for Use (Mar. 12, 2015), 26 pages.
Mega Electronics Ltd., "800778 eMotion Faros Series Manual 2.3.0," (Apr. 10, 2017), 42 pages.
Vital Signum, "Beat2Phone User Guide," Version 1.1, Android, [online], Retrieved from the Internet: www.manualslib.com, (Oct. 2017), 12 pages.
VitalConnect, "VitalPatch," [Online], Retrieved from the Internet: https://web.archive.org/web/20170830052411/https:/vitalconnect.com/solutions/vitalpatch/, (Aug. 30, 2017), 3 pages.
Wayback Machine, "HeartyPatch," [online], Retrieved from the Internet: https://web.archive.org/web/20180530180927/https:/www.crowdsupply.com/protocentral/heartypatch, (May 30, 2018), 16 pages.
Written Opinion of the International Preliminary Examining Authority for International Application No. PCT/JP2020/009803 dated Jan. 14, 2021, 7 pages.
Written Opinion of the International Preliminary Examining Authority for International Application No. PCT/JP2020/009815 dated Jan. 14, 2021, 9 pages.
Communication dated Mar. 13, 2024 issued in the corresponding European Patent Application No. 20704617.8.

* cited by examiner

ELASTIC WEARABLE SENSOR

CROSS-REFERENCE TO RELATED APPLICATIONS

This application is a U.S. National Stage Application under 35 U.S.C. § 371 of International Application No. PCT/JP2020/002521, filed Jan. 24, 2020, entitled "ELASTIC WEARABLE SENSOR" which claims priority to and the benefit of U.S. Provisional Application No. 62/796,435, filed Jan. 24, 2019, entitled "Elastic Wearable Sensor," the entire contents of each of which is hereby expressly incorporated by reference for all purposes.

TECHNICAL FIELD

Some embodiments described herein relate generally to systems, methods, and apparatus for elastic wearable sensors that are able to accommodate skin deformation.

BACKGROUND ART

The non-invasive measurement of electrical potential differences (e.g., biosignals) between locations on the skin of a human or animal may be used to diagnose and monitor a condition of the human or animal. For example, the measurement of electrical potential differences between locations on the skin may be used in performing an electrocardiogram (ECG), an electroencephalogram (EEG), and an electromyogram (EMG). The measurement of the electrical potential difference between locations on the skin may include coupling an electrode at each location, electrically coupling each electrode to an electronics module, and comparing the electric potential measured at the location of at least one of the electrodes to a reference electric potential (e.g., the electric potential measured at the location of another electrode).

Furthermore, in in vivo telemetry applications, sensors on the skin of a human or animal may be configured to communicate with implanted or digested devices (e.g., digital medicines). For example, an implanted or digested device disposed within a patient may be able to communicate signals to a surface of the patient via body tissue. Using the body tissue as a conductive transmission medium, the signal may be detectable on the surface of the patient as an electrical potential difference.

To detect events that may occur only occasionally, a sensor device may be attached to the surface of the patient for an extended period of time (e.g., hours or days). For example, for the detection of occasional cardiac arrhythmias, a Holter monitoring device may be attached to a patient for twenty-four hours or longer.

Human skin, however, is highly elastic. For example, a typical range for the elastic constant of human skin is 0.1 to 2 MPa and may depend on factors including body location and age. Furthermore, natural movement of the patient may result in significant compressive and tensile skin strain, sometimes even in the range of 30-50% in the chest region, for example. Maintaining attachment between electrodes and human skin can present challenges, especially if the skin moves significantly due to patient movement and if the electrodes are intended to remain attached over an extended period of time (e.g., hours, days, weeks). Skin strain may cause stress on the interface between the adhesive and the skin of the patient, causing discomfort to the patient and weakening the adhesion. The use of strong adhesives used to attach the sensor device to the patient's skin may be uncomfortable for the patient due to lack of breathability and/or causing skin irritation.

Thus, there is a need for a sensor systems, methods, and apparatus that can accommodate movement-induced skin deformations while also improving adhesion durability, being breathable, and improving conformality with the skin surface.

SUMMARY OF INVENTION

In some embodiments, a system includes a first assembly, a second assembly, and a connecting member. The first assembly includes a first electrode and a first adhesive portion. The first assembly is configured to be coupled to a surface of a patient via the first adhesive portion. The second assembly includes a second electrode and a second adhesive portion. The second assembly is configured to be coupled to the surface of the patient via the second adhesive portion. The connecting member has a first end, a second end, and a third adhesive portion. The first end is coupled to the first assembly and the second end is coupled to the second assembly. The connecting member is configured to transition between a first configuration and a second configuration. The distance between the first end and the second end of the connecting member in the first configuration is a first distance. The distance between the first end and the second end of the connecting member in the second configuration is a second distance. The second distance is different from the first distance. The connecting member may be configured to be coupled to the surface of the patient via the third adhesive portion in both the first configuration and the second configuration.

DESCRIPTION OF EMBODIMENTS

Figure 1:
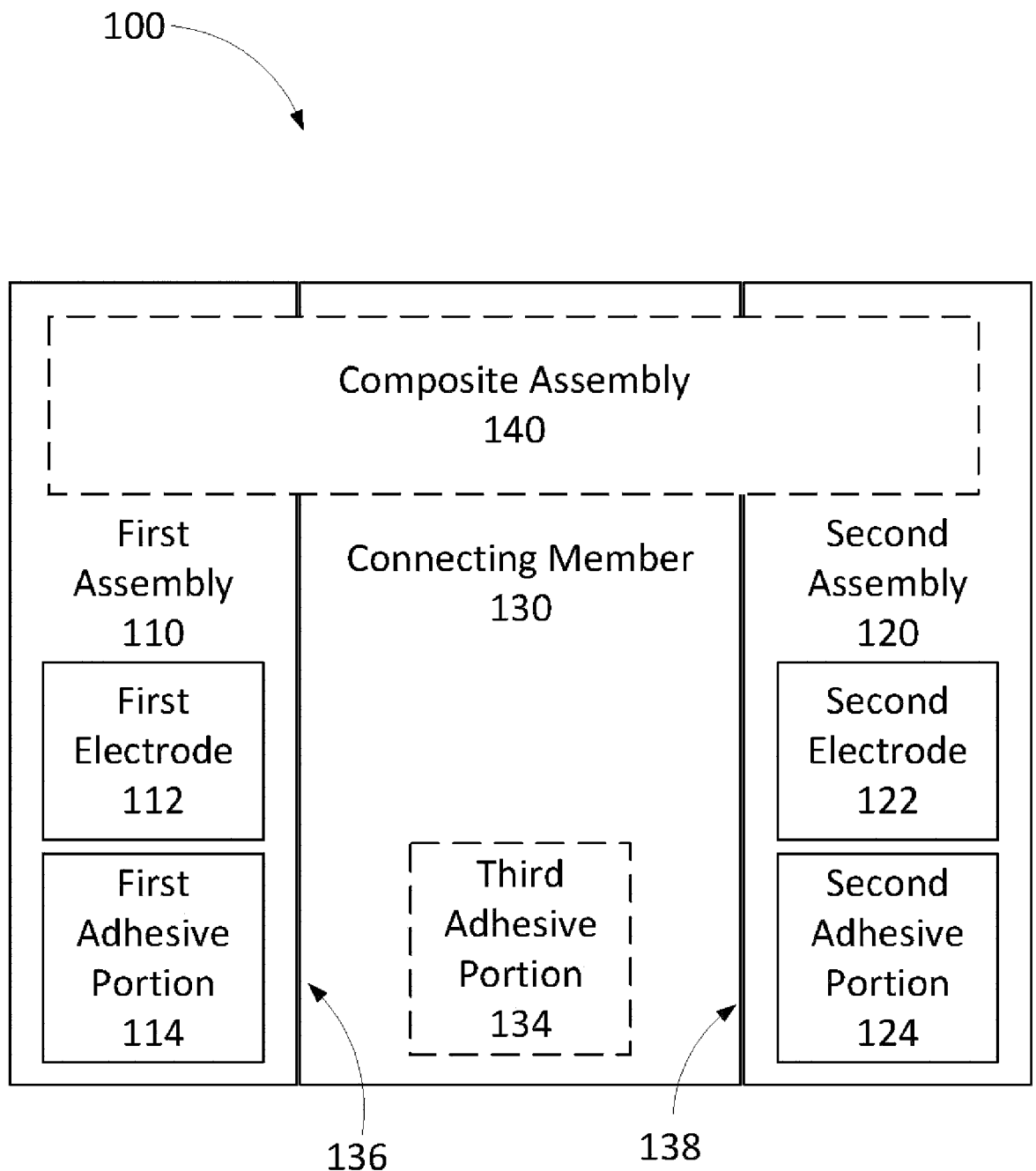
FIG. 1 is a schematic illustration of a sensor system, according to an embodiment.

In some embodiments, a system includes a first assembly, a second assembly, and a connecting member. The first assembly includes a first electrode and a first adhesive portion. The first assembly is configured to be coupled to a surface of a patient via the first adhesive portion. The second assembly includes a second electrode and a second adhesive portion. The second assembly is configured to be coupled to the surface of the patient via the second adhesive portion. The connecting member has a first end, a second end, and a third adhesive portion. The first end is coupled to the first assembly and the second end is coupled to the second assembly. The connecting member is configured to transition between a first configuration and a second configuration. The distance between the first end and the second end of the connecting member in the first configuration is a first distance. The distance between the first end and the second end of the connecting member in the second configuration is a second distance. The second distance is different from the first distance. The connecting member may be configured to be coupled to the surface of the patient via the third adhesive portion in both the first configuration and the second configuration.

In some embodiments, a system includes a first assembly, a second assembly, and a composite assembly. The first assembly includes a first electrode and a first housing. The first assembly is configured to be coupled to a surface of a patient's skin via a first adhesive portion. The second assembly includes a second electrode and a second housing. The second assembly is configured to be coupled to a surface of a patient's skin via a second adhesive portion. The composite assembly includes a processor and a composite board having a flexible portion. The flexible portion has a first end and a second end. The processor is disposed between the first electrode and the first housing. The composite assembly is configured to transition from a first configuration to a second configuration. A distance between the first end and the second end of the flexible portion in the first configuration is a first distance and a distance between the first end and the second end of the flexible portion in the second configuration is a second distance different from the first distance.

In some embodiments, a system includes a first assembly, a second assembly, and a composite assembly. The first assembly includes a first electrode and a first adhesive portion. The first assembly is configured to be coupled to a surface of a patient via the first adhesive portion. The second assembly includes a second electrode and a second adhesive portion. The second assembly is configured to be coupled to a surface of a patient via the second adhesive portion. The composite assembly has a flexible portion. The flexible portion has a first end, a second end, and a plurality of layers. Each layer from the plurality of layers has a conductor extending between the first end and the second end. The first end is coupled to the first assembly and the second end is coupled to the second assembly. The composite assembly is configured to electrically couple the first assembly with the second assembly. The flexible portion is configured to transition from a first configuration to a second configuration. A distance between the first end and the second end of the flexible portion in the first configuration is a first distance. A distance between the first end and the second end of the flexible portion in the second configuration is a second distance different from the first distance. The flexible portion is configured to be coupled to a surface of a patient via a third adhesive portion in both the first configuration and the second configuration.

FIG. 1 is a schematic illustration of a sensor system 100. The system 100 may be, for example, formed as a patch. As shown in FIG. 1, the system 100 includes a first assembly 110, a second assembly 120, and a connecting member 130. The first assembly 110 includes a first electrode 112 and a first adhesive portion 114. The first assembly 110 is configured to be coupled to a surface of a patient via the first adhesive portion 114. The second assembly 120 includes a second electrode 122 and a second adhesive portion 124. The second assembly 120 is configured to be coupled to the surface of the patient via the second adhesive portion 124. The connecting member 130 has a first end 136 and a second end 138. The first end 136 is coupled to the first assembly 110 and the second end 138 is coupled to the second assembly 120. The first electrode 112 and the second electrode 122 may be galvanic or non-galvanic.

The connecting member 130 is configured to transition between a first configuration and a second configuration. The distance between the first end 136 and the second end 138 of the connecting member 130 in the first configuration may be a first distance. The distance between the first end 136 and the second end 138 of the connecting member 130 in the second configuration may be a second distance. The second distance is different from the first distance. For example, the second difference may be greater than or less than the first distance.

In some implementations, the connecting member 130 includes a third adhesive portion 134. The connecting member 130 can be configured to be coupled to the surface of the patient via the third adhesive portion 134 in both the first configuration and the second configuration. In some implementations, the connecting member 130 can be configured to be coupled to the surface of the patient via the third adhesive portion 134 during a transition from the first configuration to the second configuration and/or during a transition from the second configuration to the first configuration. In some implementations, the connecting member 130 can include a skin-facing surface. The skin-facing surface can extend from the first end 136 to the second end 138 of the connecting member 130. The third adhesive portion 134 may be disposed on all or a portion of the skin-facing surface.

In some embodiments, the system 100 includes a composite assembly 140. The composite assembly 140 can be included in and/or otherwise form an integrated circuit (IC), a printed circuit board (PCB) assembly including a printed circuit board, an application-specific integrated circuit (ASIC), or any other suitable electrical circuit structure. For example, the composite assembly 140 can include a composite board (e.g., a printed circuit board) and any suitable electronic components. The electronic components can be electrically coupled to the composite board. The electronic components can be coupled to conductors (e.g., conductive traces) of the composite board via, for example, soldering, spot welding, conductive adhesives, and/or via a tab contact. The conductive traces can be etched into the composite board. The electronic components can include, for example, a processor, an energy storage device, a memory, a transmitter, and/or a receiver. The electronic components can also include, for example, biosignal acquisition electronic components such as an analog front-end (e.g., a preamplifier) and/or an analog-to-digital converter. The energy storage device can include, for example, a battery or a capacitor. In some implementations, the energy storage device can include a coin cell battery. In some implementations, the transmitter and/or the receiver can include an antenna and can be able to communicate wirelessly via, for example, Bluetooth(trademark), near-field communication, and/or WiFi. In some implementations, the composite assembly 140, the first electrode 112, and the second electrode 122 can collectively be configured to perform any suitable type of monitoring such as ECG, EEG, EMG, and/or galvanic skin response (GSR) monitoring. In some implementations, the composite assembly 140 can include all of the electronic components necessary for the system 100 to be fully operational to perform a monitoring operation (e.g., ECG) and transmit the data gathered via the first electrode 112 and the second electrode 122 wirelessly to any suitable receiving device (e.g., an external computer or smart phone).

In some implementations, the composite board of the composite assembly 140 can be a one-piece monolithic structure. In some implementations, the composite board can be formed of an insulator. The insulator may include, for example, polyimide. In some implementations, the composite board can be formed of any suitable material such as, for example, polyethylene terephthalate (PET) or polyethylene naphthalate (PEN). In some implementations, the composite assembly 140 can include any number of conductive layers that are physically and electrically separated by a corresponding number of insulating layers. The insulating layers can be formed from an insulating and/or dielectric material such as polyimide, fiberglass, cotton, silicone, and/or the like that can be bound by any suitable resin material (e.g., epoxy, polyimide, or the like). Thus, the insulating layers can be, for example, dielectric layers and/or core layers that can physically and electrically separate the conductive layers.

In some implementations, the composite board can be a laminated composite board. For example, the conductive layers can be, for example, relatively thin conductive sheets that are disposed on at least one surface of an insulating layer (i.e., a core layer). For example, the conductive layer can be copper, silver, aluminum, gold, zinc, tin, tungsten, graphite, conductive polymer, and/or any other suitable conductive material. In this manner, the conductive sheet can be masked and the undesired portions of the conductive sheet can be etched away, thereby leaving a desired set of conductive traces. Moreover, the composite assembly 140 can include any number of alternately stacked insulating layers and conductive layers and can include a set of electrical interconnects (e.g., vias, pressed pins, bus bars, terminals, etc.) that can selectively place the conductive layers in electrical contact. Thus, the composite assembly 140 can be configured to carry a current (e.g., associated with power distribution, a signal carrying information and/or induced by a magnetic source) along a length of the conductive traces.

In some implementations, the composite board can include conductors (e.g., conductive traces) printed on one or both sides of the composite board such that the composite assembly 140 can be configured to carry a current (e.g., associated with power distribution, a signal carrying information and/or induced by a magnetic source) along a length of each of the conductors. For example, the composite board can include a carrier film (e.g., a PET or PEN carrier film) onto which conductors can be printed via an additive manufacturing process. In some implementations, the conductors can be formed by printed silver and/or printed copper. In some implementations, the composite board may include any number of layers having conductors printed on one or both sides, and each of the layers having conductors can be physically and electrically separated from one another by a corresponding number of insulating layers (e.g., the layers having conductors and the insulating layers can be alternately stacked). In some implementations, the composite assembly 140 can include a two-layer conductor structure. The two-layer conductor structure can be formed via multi-layer printing. An insulator can be printed at the location of any conductor crossings. In some implementations, the two-layer conductor structure can be formed using a through-substrate-via approach.

In some implementations, the composite assembly 140 can include a number of composite boards or board layers. Each of the composite boards can be monolithically formed. The composite boards or board layers can be arranged relative to one another in any suitable arrangement (e.g., stacked).

In some implementations, the connecting member 130 (e.g., one or more composite boards of the composite assembly) can be sufficiently flexible such that the connecting member 130 can change in shape while remaining coupled to the first assembly 110 and the second assembly 120 when the first assembly 110 is moved relative to the second assembly 120 (e.g., due to movement of the skin locations to which the first assembly 110 and the second assembly 120 are coupled). Thus, the connecting member 130 can accommodate skin deformations by reducing stress at the skin-adhesive interface compared to a connecting member with an undeforming shape, causing better adhesion durability and better wear comfort for the user. In some implementations, the connecting member 130 may include a number of portions (e.g., arranged in series) configured to move relative to one another when the first assembly 110 is moved relative to the second assembly 120 such that the connecting member 130 remains coupled to the first assembly 110 and the second assembly 120.

In some implementations, the connecting member 130 (e.g., one or more composite boards of the composite assembly) can be sufficiently flexible such that the connecting member 130 can deform from an initial configuration or shape when the first assembly 110 is moved relative to the second assembly 120 (e.g., due to movement of the skin locations to which the first assembly 110 and the second assembly 120 are coupled). In some implementations, the connecting member 130 (e.g., one or more composite boards of the composite assembly), can be sufficiently elastic such that the connecting member 130 can function as a spring arranged between the first assembly 110 and the second assembly 120, allowing for expansion and contraction of the length of the connecting member 130 relative to an equilibrium or undeformed length.

In some implementations, the connecting member 130 can have rigid or semi-rigid end portions and a flexible portion extending between the ends. For example, the end portions can be made of rigid or semi-rigid PCB material (e.g., FR4) and the flexible portion between the ends can be formed of polyimide. In some implementations, the portions of a composite board of the composite assembly 140 included in the first assembly 110 and/or the second assembly 120 can be rigid or semi-rigid (e.g., formed of FR4-type PCB), and a portion of the composite board included in the connecting member 130 can be flexible (e.g., formed of a flexible PCB including, for example, polyimide). In some implementations, the first end 136 and the second end 138 of the connecting member 130 can include or be coupled to a first end and a second end of a flexible portion of a composite board included in the composite assembly 140. In some implementations, a composite board of the composite assembly 140 can be fully flexible such that a portion of the composite board included in the first assembly 110, a portion of the composite board included in the second assembly 120, and a portion of the composite board included in the connecting member 130 are all flexible. For example, the composite board may be formed as a monolithic flexible structure.

As shown in FIG. 1, a portion of the composite assembly 140 can be included within or coupled to the first assembly 110, the second assembly 120, and/or the connecting member 130. For example, a deformable portion of the composite board of the composite assembly can be included in the connecting member 130, and each of the electronic components can be included in the first assembly 110 or the second assembly 120 and coupled to portions of the composite board included in the first assembly or the second assembly 120. For example, the energy storage device can be included in the second assembly 120 and coupled to the composite board 140, and other electronic components such as the processor, memory, transmitter, and/or receiver can be included in the first assembly 110 and coupled to the composite board 140. The connecting member 130 can include only a portion (also referred to herein as a "flexible portion") of the composite board. The flexible portion of the composite board may have a first end and a second end coupled to the first end 136 and the second end 138, respectively. In some implementations, at least a portion of the composite board of the composite assembly 140 is flexible and/or elastic.

In some implementations, the connecting member 130 or a portion of the connecting member 130 can be flexible. In some implementations, the connecting member 130 or a portion of the connecting member 130 can be inelastic and/or rigid. In some implementations, the connecting member 130 or a portion of the connecting member can be elastic. In some implementations, the first configuration of the connecting member 130 can be an undeformed configuration toward which the connecting member 130 is elastically biased. The second configuration of the connecting member 130 can be a deformed configuration different from the undeformed configuration. The connecting member 130 can be configured to be deformed from the first configuration to the second configuration when a force is applied to the first end 136 and/or the second end 138 of the connecting member 130. The connecting member 130 can be configured to transition from the second configuration to the first configuration when the force is removed.

The connecting member 130 can have any suitable shape. The portion of the composite assembly 140 (e.g., a portion of the composite board of the composite assembly 140) included within or forming the connecting member 130 (e.g., a flexible portion of the composite board of the composite assembly 140) can have any suitable shape. The shape of the connecting member 130 can correspond to the shape of a portion of the composite board included in the connecting member 130. In some implementations, at least a portion of the composite board of the composite assembly 140 is biased toward a first undeformed configuration such that the connecting member 130 is biased toward the first configuration.

In some implementations, the connecting member 130 can have an arched or curved shape extending from the first end 136 to the second end 138. In some implementations, the connecting member 130 can have a shape including a pattern with any suitable number of repeating portions. For example, the connecting member 130 can have a serpentine shape, a sinusoidal shape, a zig-zag shape, a repeating sawtooth shape, a repeating triangle shape, and/or any combination of shapes. In some implementations, the connecting member 130 can be shaped as a sinusoidal wave including two, three, four, five, or more periods. In some implementations, the connecting member 130 can be shaped as a sinusoidal wave having any suitable number of periods with any suitable wavelength and/or amplitude. For example, the connecting member 130 may be shaped to include one, two, three, four, five, or more periods of a sinusoidal wave at any suitable wavelength, amplitude, and/or frequency. In some implementations, the connecting member 130 can be shaped as a sinusoidal wave having multiple periods having varying wavelengths and/or amplitudes from the first end 136 to the second end 138 of the connecting member 130. In some implementations, the connecting member 130 can have a first sinusoidal shape having a first frequency in the first configuration and a second sinusoidal shape having a second frequency in the second configuration, the second frequency different from (e.g., larger or smaller than) the first frequency.

In some implementations, the connecting member 130 can include a number of inelastic segments coupled together by elastic portions. For example, the connecting member 130 can include a first segment, a second segment, and an elastic hinge coupling the first segment to the second segment. In some implementations, the elastic hinge can form a curved portion and the first segment and the second segment may each be curved or straight. In some implementations, the curved portion can include an arc segment. In some implementations, the elastic hinge can form an angled portion and the first segment and the second segment can each be straight portions. In some implementations, for example, the elastic hinge, first segment, and second segment can be arranged such that the first segment is arranged at an angle ranging from about 5° to about 120° relative to the second segment in the first, undeformed configuration. In some implementations, the connecting member 130 can have a number of elastic hinges coupling segments of the connecting member 130 to one another. For example, the connecting member 130 can include three segments, four segments, five segments, seven segments, or any other suitable number of segments, each segment being coupled to an adjacent segment by an elastic hinge.

In some implementations, the connecting member 130 can have a length (e.g., a distance from the first end 136 to the second end 138) and a width (e.g., a distance from an outermost edge of the connecting member 130 extending in a first direction extending perpendicularly relative to a line extending between the first assembly 110 and the second assembly 120 to an outermost edge of the connecting member 130 extending in a second direction opposite the first direction). The length of the connecting member 130 may be measured in an X-direction and the width may be measured in a Y-direction perpendicular to the X-direction. The connecting member 130 can have a first overall length and a first width in the first configuration and a second length and a second width in the second configuration. When the first assembly 110 and the second assembly 120 are closer to each other in the second configuration than in the first configuration, the second length may be smaller than the first length and the second width may be greater than the first width. When the first assembly 110 and the second assembly 120 are farther from each other in the second configuration than in the first configuration, the second length may be greater than the first length and the second width may be smaller than the first width.

In some implementations, the connecting member 130 can have the same overall shape (e.g., a zig-zag shape or a sinusoidal shape) in the first configuration and the second configuration, and the shape can be compressed or expanded in the second configuration compared to the first configuration. For example, an angle between two segments coupled via an elastic hinge of the connecting member 130 can be a first angle in the first configuration and a second angle in the second configuration. When the first assembly 110 and the second assembly 120 are closer to each other in the second configuration than in the first configuration, the second angle may be smaller than the first angle. When the first assembly 110 and the second assembly 120 are farther from each other in the second configuration than in the first configuration, the second angle may be greater than the first angle.

The connecting member 130 can have any suitable thickness along the length of the connecting member 130 and/or height relative to a bottom surface of the connecting member 130. In some implementations, the thickness of the connecting member 130 may vary along the length of the connecting member 130 (e.g., one or more portions of the connecting member 130 may be thicker compared to more narrow portions of the connecting member 130). The height of the connecting member 130 can be a distance extending in a Z-direction which is perpendicular to both the X and Y-directions. The thickness can be a distance disposed in a plane including the X and Y-directions (as describe in more detail below). In some embodiments, the thickness of the connecting member 130 and/or the height of the connecting member 130 can be sufficiently small such that the connecting member 130 is sufficiently elastic (e.g., has a sufficiently small spring constant) to expand and contract based on movement (e.g., deformation such as flexing) of the skin to prevent discomfort and/or detachment of the system 100 from the skin. For example, the thickness of the connecting member 140 and/or the height of the connecting member 130 can be sufficiently small such that the connecting member 130 has enough elasticity from a first end 136 of the connecting member 130 to a second end 138 of the connecting member 130 to expand and contract based on movement of the skin locations to which the first assembly 110 and the second assembly 120 are attached (i.e., such that skin elasticity can be accommodated by the connecting member 130). As an example, the surface of the skin to which the system 100 can be coupled may have an elasticity in the range of 0.1 to 2 MPa, and the connecting member 130 can have an elasticity equivalent to or less than the elasticity of the surface of the skin to which the system 100 is coupled such that the connecting member 130 can expand and contract in the X-direction with the deformation of the skin to which the first assembly 110 and the second assembly 120 is attached. In some implementations, the thickness of the connecting member 130 can be, for example, equal to or less than 100 µm. In some implementations, the height of the connecting member 130 can be, for example, equal to or less than 36 µm. In some implementations, the spring constant of the connecting member 130 (in the X-direction) can increase proportionally to a cube of the thickness of the connecting member 130 and linearly with respect to the height of the connecting member 130.

In some implementations, the first assembly 110 includes a first housing and the second assembly 120 includes a second housing. The connecting member 130 may optionally include a third housing. In some implementations, the first adhesive portion 114 can be disposed on a skin-facing surface of the first housing and the second adhesive portion 124 can be disposed on a skin-facing surface of the second housing. The third adhesive portion 134 can be disposed on a skin-facing surface of the third housing. The skin-facing surface of the first housing, the skin-facing surface of the second housing, and the skin-facing surface of the third housing can collectively form a continuous border along the outer edges of the system 100 configured to couple to a surface of a patient (e.g., skin). The first adhesive portion 114 can partially or fully surround the first electrode 112 and the second adhesive portion 124 can partially or fully surround the second electrode. In some implementations, the third housing can have a shape corresponding to the connecting member 130. The skin-facing surface of the third housing has sufficient surface area such that the third adhesive portion 134 can have a large enough surface area to maintain attachment between the connecting member 130 and the surface of the patient and to maintain conformality of the system 100 with the surface of the patient. By maintaining the attachment between the connecting member 130 and the surface of the patient, the third adhesive portion 134 can reduce motion artifacts (e.g., noise caused by movement of conductive traces in the connecting member 130) in the signal recorded by the composite assembly 140.

In some implementations, the first housing, the second housing, and the third housing collectively form a cover layer and/or a bottom layer. The cover layer can be shaped and sized such that the cover can protect the composite assembly 140 when the system 100 is disposed on a surface of a patient. In some implementations, the bottom layer can be shaped and sized such that the composite assembly 140 can be disposed between the cover layer and the bottom layer and the bottom layer can be disposed between the composite assembly 140 and the surface of the patient when the system 100 is coupled to the surface of the patient. The bottom surface can be coupled to the surface of the patient via the first adhesive portion 114, the second adhesive portion 124, and, optionally, the third adhesive portion 134. In some implementations, the bottom layer can define a first opening configured such that the first electrode 112 can contact the surface of the patient through the first opening and a second opening configured such that the second electrode 122 can contact the surface of the patient through the second opening. In some implementations, the cover layer may be monolithically or integrally formed. In some implementations, the bottom layer may be monolithically or integrally formed.

In some implementations, the cover layer and the bottom layer can protect the system 100 from external effects (e.g., liquid (e.g., water or sweat) or mechanical impacts). In some implementations, the cover layer and the bottom layer can provide a sealed enclosure surrounding the composite assembly 140 such that the composite assembly 140 is protected from water during activities of the user such as, for example, showering or swimming. In some implementations, the bottom layer can include an adhesive on a side of the bottom layer facing the composite assembly 140 such that the bottom layer can be secured to the composite assembly 140. In some implementations, the system 100 can be waterproof and/or breathable for skin comfort. In some implementations, the system 100 can include hydrogel disposed on a skin-contacting side of the first electrode 112 and on a skin-contacting side of the second electrode 124. In some implementations, the hydrogel can include cut pads (e.g., cut from a hydrogel sheet). In some implementations, the hydrogel can be in the form of a dispensable gel. In some implementations, rather than including hydrogel, the first electrode 112 and the second electrode 124 can be dry electrodes configured to couple directly to a surface of the patient.

The cover layer and the bottom layer can be formed of, for example, medical-grade materials (e.g., medical-grade materials manufactured by 3M and/or Adhesives Research). In some implementations, the cover layer and/or the bottom layer can be formed of a multi-layer material including adhesive layers. In some implementations, the adhesive includes synthetic rubber, acrylates, and/or silicones. In some implementations, the layers can include layers formed of polymers, PET, polyethylene (PE), polyurethane (PU), and/or polyamide (PA). The cover layer and the bottom layer can include film, non-woven materials, or a combination. In some implementations, the cover layer and/or the bottom layer can be formed of polyurethane materials combines with acrylic adhesives such that the cover layer and/or the bottom layer are waterproof, breathable, and minimize skin irritation of the user.

In some implementations, the composite assembly 140 can include multiple electrical connections between electrical components disposed in the first assembly 110 and the second assembly 120. For example, the connecting member 130 can include multiple electrical connections extending from the first end 136 of the connecting member 130 to the second end 138 of the connecting member 130. In some implementations, for example, the connecting member 130 can include a composite board and one or more traces can be etched into the composite board. In some implementations, the connecting member 130 can include a number of stacked composite boards with at least one conductive trace etched into each composite board. In some implementations, the composite assembly 140 can include a multi-layer composite board, an elastically deformable portion of the multi-layer composite board included in the connecting member 130. For example, a first laminated composite layer having a first trace can be coupled to a second laminated composite layer having a second trace such that the first laminated composite layer and the first trace are vertically higher (e.g., in the Z-direction) than the second laminated composite layer and the second trace. A third laminated composite layer having a third trace can be coupled to the second laminated composite layer such that the second laminated composite layer and the second trace are vertically higher than the third laminated composite layer and the third trace. The traces of the laminated composite layers can be electrically isolated by insulative material forming the laminated composite layers. In some implementations, the traces of each of the layers of the multi-layer composite board can be electrically coupled via, for example, vias in any suitable arrangement. In some implementations, the multiple electrical connections may include electrical wiring.

The third adhesive portion 134 can be coupled to any suitable portion of the connecting member 130. For example, the third adhesive portion 134 can be disposed on a skin-facing surface of one or more of the flexible hinges such that the skin-facing surface of one or more of the flexible hinges may be coupled to a surface of a patient. Additionally or alternatively, the third adhesive portion 134 can be disposed on a skin-facing surface of a rigid segment coupled to a flexible hinge such that the rigid segment is coupled to a surface of a patient. In some implementations, the third adhesive portion 134 can be disposed in one location or more than one location on a skin-facing surface of the connecting member 130. The third adhesive portion 134 can include discrete adhesive portions disposed in various locations (e.g., on flexible hinges and/or segments connecting flexible hinges to other segments or the first assembly 110 or second assembly 120) on a skin-facing surface of the connecting member 130.

The first adhesive portion 114, the second adhesive portion 124, the third adhesive portion 134, and any of the adhesives described herein can include any suitable type of adhesive. For example, the adhesive can be synthetic rubber, acrylates, and/or silicones. The adhesives can be applied in any suitable pattern.

In some implementations, the system 100 can accommodate movement-induced skin deformations (e.g., due to skin flexing or tension) while continuing to operate to measure differences in electrical potential between discrete skin locations such that weaker adhesives or smaller adhesive interfaces may be utilized compared to a rigid system without an elastic connecting member. Furthermore, the system 100 can be more breathable than rigid systems due to the reduced skin surface area covered with adhesive. For example, the first assembly 110 can be coupled to a first location on a surface of a patient via the first adhesive portion 114 and the second assembly 120 can be coupled to a second location on the surface of the patient via the second adhesive portion 124 when the first location and the second location are in an initial configuration relative to each other. If the first location on the surface of the patient moves closer to the second location on the surface of the patient (e.g., due to patient movement), the first assembly 110 can move toward the second assembly 120, decreasing the distance between the first end 136 of the connecting member 130 and the second end 138 of the connecting member 130. The movement of the first assembly 110 toward the second assembly 120 can cause the connecting member 130 to be compressed. If the first location on the surface of the patient moves farther from the second location on the surface of the patient (e.g., due to patient movement), the first assembly 110 can move farther from the second assembly 120, increasing the distance between the first end 136 of the connecting member 130 and the second end 138 of the connecting member 130. The movement of the first assembly 110 away from the second assembly 120 can cause the connecting member 130 to expand. In implementations in which the connecting member 130 is coupled to a third location on the surface of the patient via the third adhesive portion 134, the portions of the connecting member 130 coupled to the third location can move relative to the first assembly 110 and the second assembly 120 based on the movement of the third location relative to the first location and the second location. If the first location and the second location return to the initial configuration, the connecting member 130 will return to the first undeformed configuration.

Figure 2A:
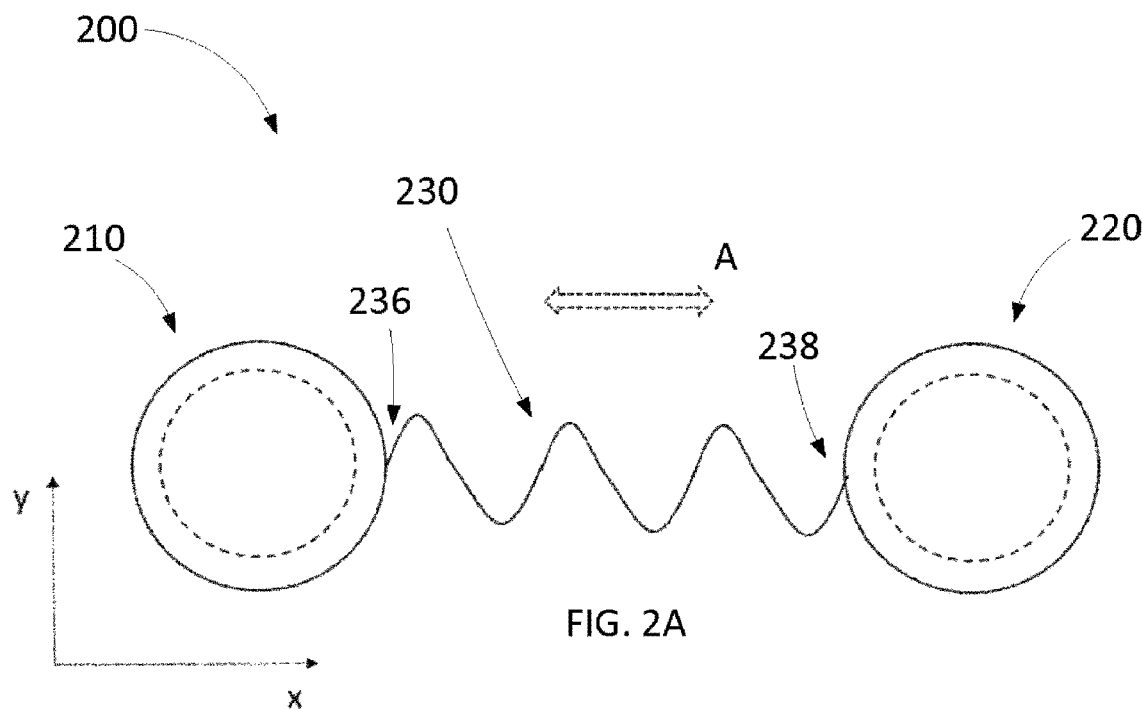
FIG. 2A is an illustration of a top view of a sensor system, according to an embodiment.

FIG. 2A is a schematic illustration of a top view of a system 200. The system 200 can be the same or similar in structure and/or function to the system 100 described above. For example, the system 200 can include a first assembly 210, a second assembly 220, and a connecting member 230, which can be the same or similar to the first assembly 110, the second assembly 120, and the connecting member 130, respectively. As shown in FIG. 2A, the connecting member 230 includes a first end 236 and a second end 238. The connecting member 230 is coupled to the first assembly 210 via the first end 236 and to the second assembly 220 via the second end 238. The connecting member 230 is configured to transition between a first configuration (shown in FIG. 2A) and a second configuration in which the first assembly 210 and the second assembly 220 are a different distance away from each other than in the first configuration. For example, when the system 200 is coupled to a patient's skin, a force (e.g., due to deformation due to skin flexing or tension) may be applied to the first assembly 210 and/or the second assembly 220 in either direction represented by the double-ended arrow A (e.g., in the X-direction) such that the length of the connecting member 230 from the first end 236 to the second end 238 is increased or decreased and the connecting member 230 is compressed or expanded. In some implementations, a force may be applied to the first assembly 210 and/or the second assembly 220 in any direction in the X-Y plane such that the length of the connecting member 230 from the first end 236 to the second end 238 is increased or decreased and the connecting member 230 is compressed or expanded.

Figure 2B:
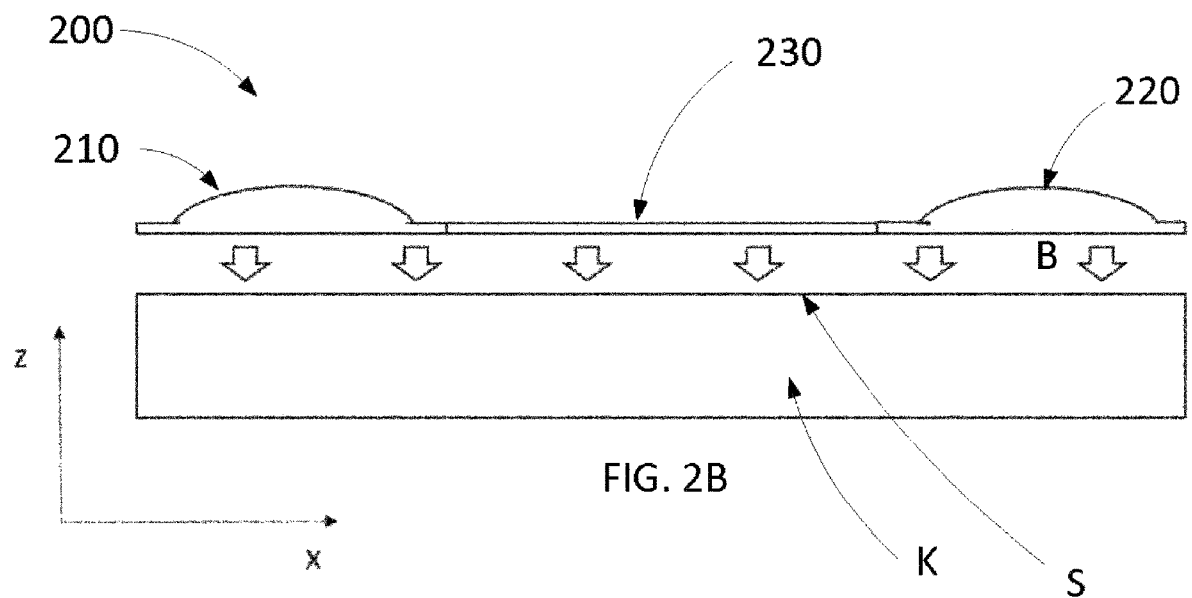
FIG. 2B is an illustration of a side view of the sensor system of FIG. 2A prior to the sensor system being coupled to a surface of a skin of a patient.

FIG. 2B is a schematic illustration of a side view of a system 200 prior to being applied to a patient's skin. As shown in FIG. 2B, the system 200 can be moved in the direction of arrows B (e.g., in the Z-direction) relative to a surface S of a skin K of a patient such that the first assembly 210, the second assembly 220, and the connecting member 230 are disposed in contact with the surface S of the skin K. As shown in FIG. 2B, the first assembly 210, the second assembly 220, and the connecting member 230 can each have a skin-facing surface that collectively forms a bottom or skin-facing surface of the system 200. The first assembly 210 can include a first electrode (not shown) and the second assembly can include a second electrode (not shown), the first and second electrode forming a portion of the bottom surface of the system 200 and configured to contact the surface S of the skin K. The first assembly 210 can be coupled to a first location on the surface S via a first adhesive portion (not shown) and the second assembly 220 can be coupled to a second location on the surface S via a second adhesive portion (now shown). The first assembly 210, the second assembly 220, and the connecting member 230 can each include a portion of a composite assembly and be configured such that the system 200 can measure a potential difference between the first location and the second location via the first electrode and the second electrode.

Figure 3A:
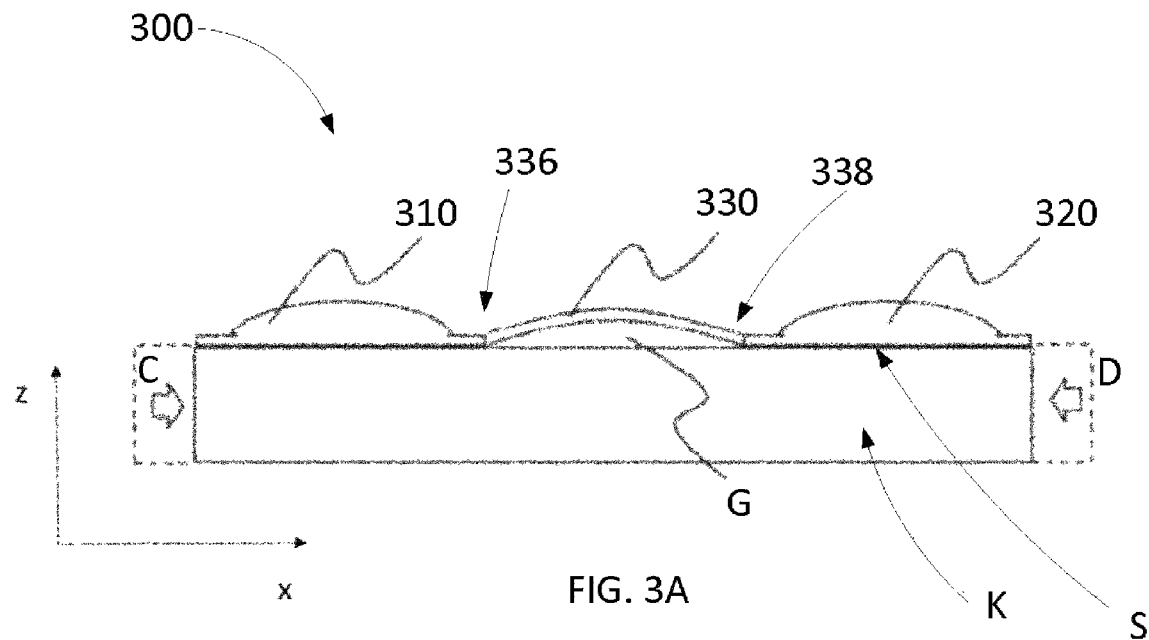
FIG. 3A is an illustration of a side view of a sensor system in a first configuration, according to an embodiment.
Figure 3B:
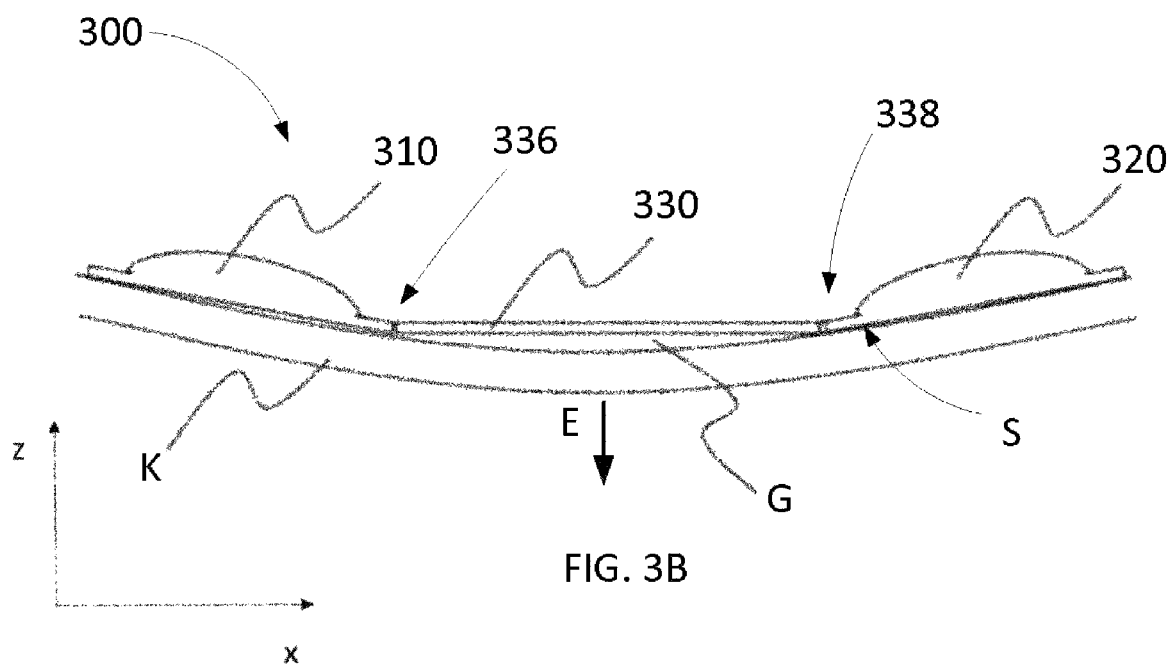
FIG. 3B is an illustration of a side view of the sensor system of FIG. 3A in a second configuration.
Figure 3C:
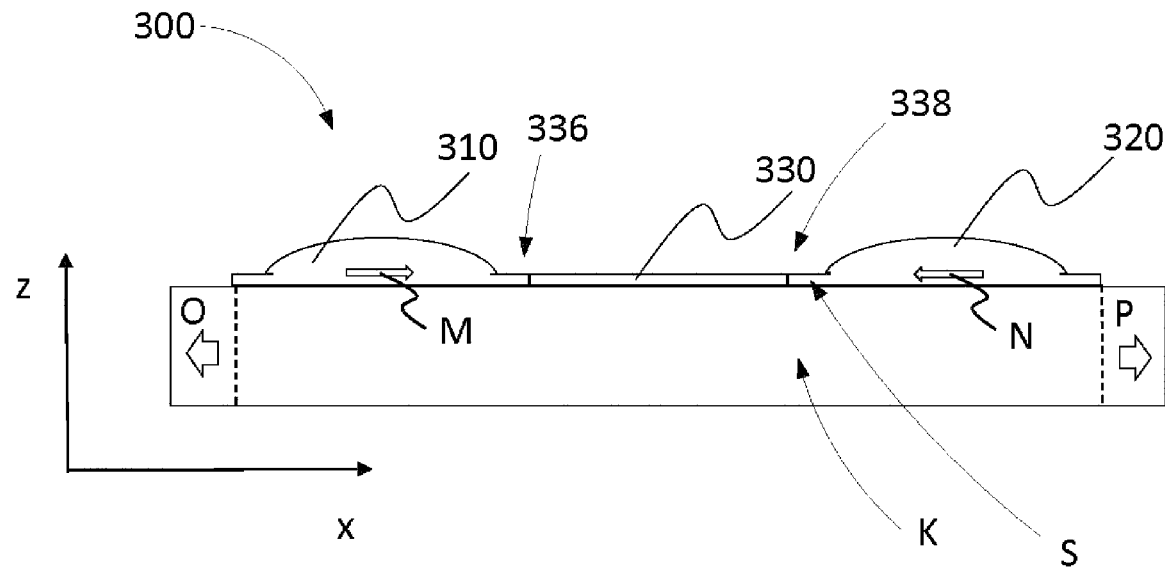
FIG. 3C is an illustration of a side view of the sensor system of FIG. 3A in a third configuration.

In some implementations, a connecting member may not include a third adhesive portion such that the connecting member is vertically movable relative to a surface of the patient. Furthermore, in some implementations, the connecting member may not have a shape allowing for expansion and contraction of the connecting member. Without a third adhesive portion and/or having an elastically deforming shape as described with respect to the connecting member 130 described above, however, the system including the connecting member may not maintain conformality with the surface of the patient's skin during patient movement. FIGS. 3A-3C are schematic illustrations of a side view of a system 300 coupled to a surface S of a skin K of a patient in a first configuration, a second configuration, and a third configuration, respectively. The system 300 may be similar in structure and/or function to any of the systems described herein. For example, the system 300 can include a first assembly 310, a second assembly 320, and a connecting member 330. The connecting member 330 has a first end 336 coupled to the first assembly 310 and a second end 338 coupled to the second assembly 320.

As shown in FIG. 3A, the first assembly 310 is coupled to the skin surface S at a first location and the second assembly 320 is coupled to the skin surface S at a second location. The skin K of the patient is under compression under a first force applied in the direction of arrow C and a second force opposite the first force applied in the direction of arrow D (i.e., opposing forces in the X-direction causing compressive skin strain). As a result of the compressive forces, the first location and the second location are pushed closer to each other, causing the first end 336 and the second end 338 of the connecting member 330 to move closer to each other. Because the connecting member 330 is not coupled to the surface S via adhesive and is not configured to be elastically deformed within a plane lying perpendicular to the surface S, the connecting member 330 may flex or bulge away from the surface S such that a gap G is defined between the connecting member 330 and the surface S. Furthermore, the compressive skin strain may also apply stress to the interface between the first assembly 310 and/or the second assembly 320 and the surface S of the skin K, potentially disrupting the interface (e.g., disrupting adhesion) and causing discomfort to the wearer of the system 300.

As shown in FIG. 3B, the first assembly 310 is coupled to the skin surface S at a first location and the second assembly 320 is coupled to the skin surface S at a second location. The skin K of the patient is deformed (e.g., under tension) under a first force applied in the direction of arrow E (i.e., in the Z-direction away from the system 300) such that the curvature of the surface S changes from a flat configuration to a curved configuration. As a result of the deformation, the first location and the second location are pushed closer to each other. Since the connecting member 330 is not coupled to the surface S via adhesive, the surface S may flex away from the connecting member 330 such that a gap G is defined between the connecting member 330 and the surface S and the connecting member 330 bulges away from the surface S. Furthermore, if the connecting member 330 is rigid, the connecting member 330 may not be able to accommodate the change in curvature of the surface S and any strain on the skin K may apply strain along the length of the system 300, inducing stresses at the interface (e.g., an adhesive interface) of the first assembly 310 and/or the second assembly 320 with the surface S of the skin K.

As shown in FIG. 3C, the first assembly 310 is coupled to the skin surface S at a first location and the second assembly 320 is coupled to the skin surface S at a second location. The skin K of the patient is under tension under a first force applied in the direction of arrow O and a second force opposite the first force applied in the direction of arrow P (i.e., opposing forces in the X-direction causing tensile skin strain). As a result of the tensile forces, the first location and the second location are pulled away from each other (i.e., the surface S is deformed via lateral expansion), causing the first end 336 and the second end 338 of the connecting member 330 to move away from each other. Because the connecting member 330 is not coupled to the surface S via adhesive and/or is not configured to be elastically deformed within a plane lying perpendicular to the surface S, the system 300 may induce a force M and a force N at the interface of the first assembly 310 and the second assembly 320, respectively, with the surface S of the skin K. The force M and the force N can disrupt the interface (e.g., disrupt adhesion via inducing a risk of adhesion loss) and can cause discomfort to the wearer of the system 300.

Figure 4A:
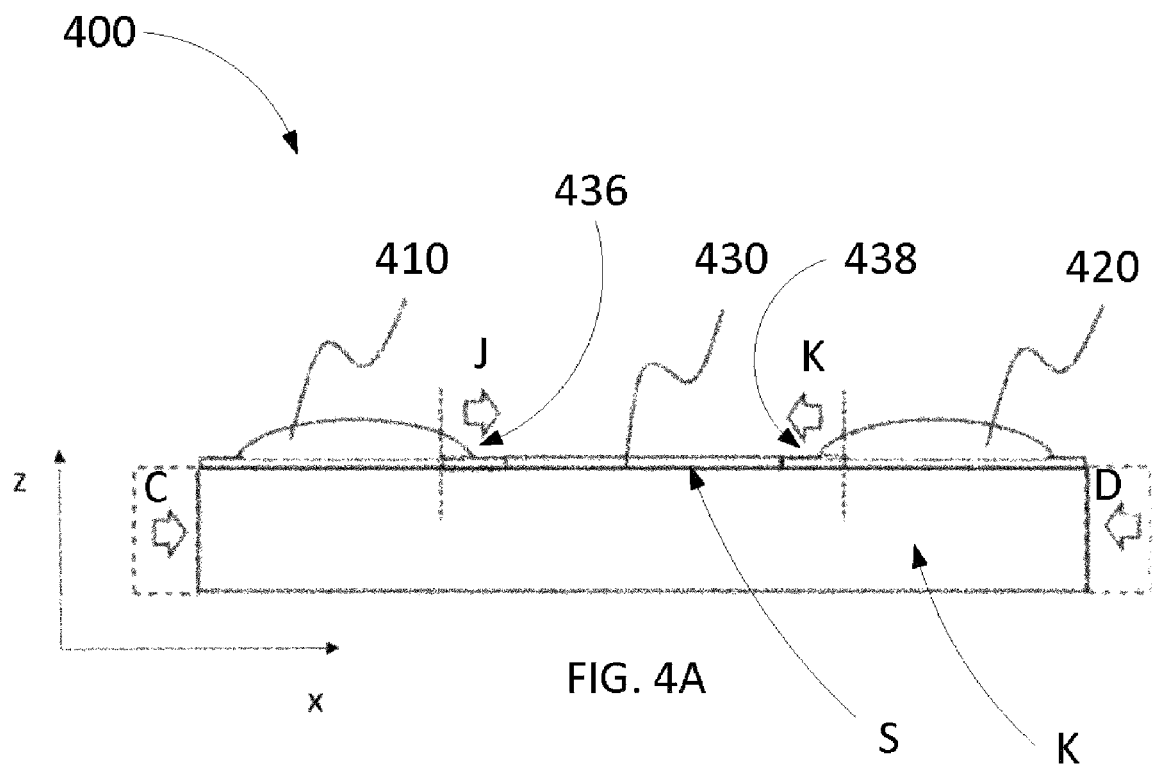
FIG. 4A is an illustration of a side view of a sensor system in a first configuration, according to an embodiment.
Figure 4B:
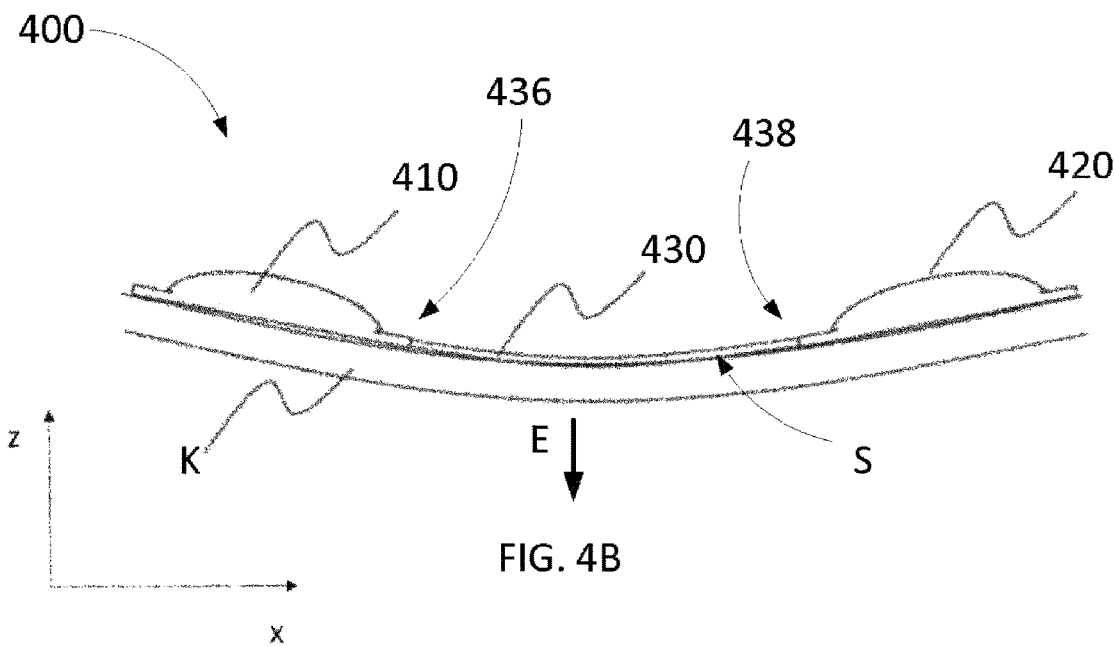
FIG. 4B is an illustration of a side view of the sensor system of FIG. 4A in a second configuration.

In some implementations, an elastic connecting member and/or a third adhesive portion coupling the elastic coupling member to the surface of a patient's skin may improve conformality between the connecting member and the surface, for example, to avoid unwanted snags of the connecting member due to the gap G and/or to avoid forces applied by the connecting member on the first or second assembly that may cause the first or second assembly to loosen from the surface. FIGS. 4A and 4B are schematic illustrations of a side view of a system 400 coupled to a surface S of a skin K of a patient in a first configuration and a second configuration, respectively. The system 400 can be similar in structure and/or function to any of the systems described herein. For example, the system 400 can include a first assembly 410, a second assembly 420, and a connecting member 430. The connecting member 430 has a first end 436 coupled to the first assembly 410 and a second end 438 coupled to the second assembly 420. As shown in FIGS. 4A and 4B, the system 400 can be able to deform with the surface S of the skin K and remain conformal with the surface S of the skin K. Furthermore, although not shown, the connecting member 430 can be coupled to the surface S via a third adhesive portion to improve conformality during deformation of the surface S.

As shown in FIG. 4A, the first assembly 410 is coupled to the skin S at a first location and the second assembly 410 is coupled to the skin S at a second location. The skin K of the patient is under compression under a first force applied in the direction of arrow C and a second force opposite the first force applied in the direction of arrow D (i.e., opposing forces in the X-direction). As a result of the compressive forces, the first location and the second location have been pushed closer to each other, causing the first end 436 and the second end 438 of the connecting member 430 to move closer to each other. Since the connecting member 430 is coupled to the surface S via adhesive and is configured to be elastically deformed within a plane lying perpendicular to the surface S, the connecting member 430 can remain conformed to the surface S such that no gap is defined between the connecting member 430 and the surface S. Thus, the system 400 can accommodate compressive deformation such that the connecting member 430 remains conformal to the surface S of the skin K with reduced stress on the adhesive interfaces between each of the first assembly 410, the second assembly 420, and the connecting member 430 with the surface S compared to a system with a non-deformable coupling member.

As shown in FIG. 4B, the first assembly 410 is coupled to the skin S at a first location and the second assembly 410 is coupled to the skin S at a second location. The skin K of the patient is under tension under a first force applied in the direction of arrow E (i.e., in the Z-direction away from the system 400). As a result of the first force, the first location and the second location have been pushed closer to each other. Since the connecting member 430 is coupled to the surface S via adhesive, the connecting member 430 remains conformed to the surface S such that no gap is defined between the connecting member 430 and the surface S.

Figure 5A:
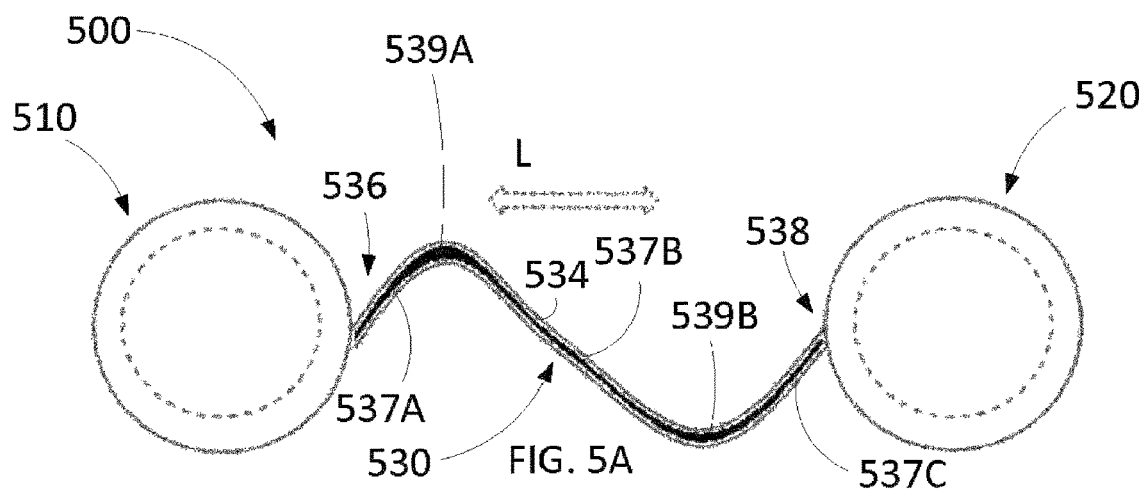
FIG. 5A is an illustration of a bottom view of a sensor system, according to an embodiment.
Figure 5B:
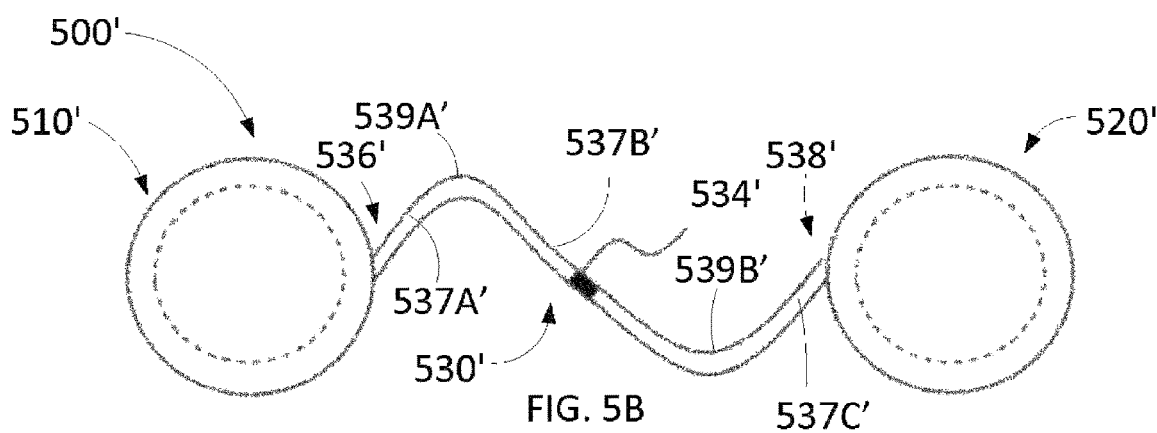
FIG. 5B is an illustration of a bottom view of a sensor system, according to an embodiment.
Figure 5C:
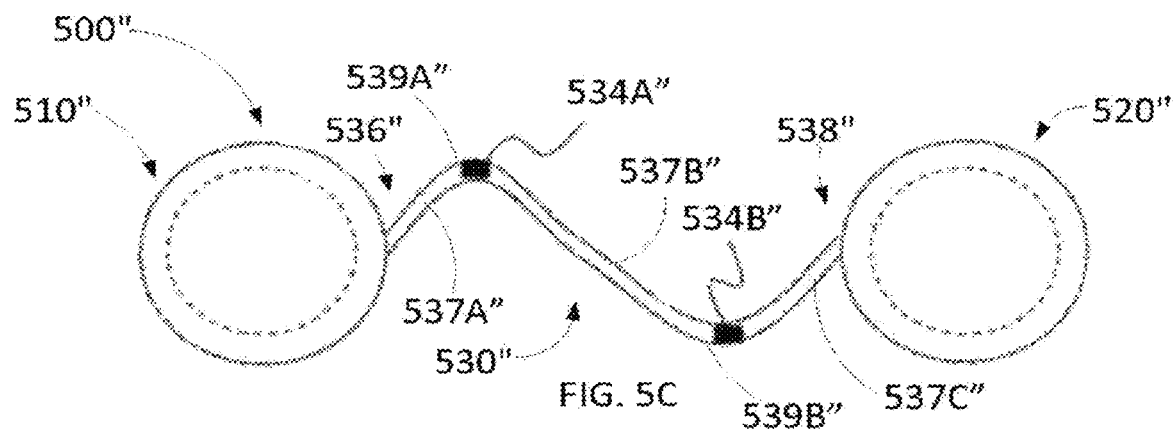
FIG. 5C is an illustration of a bottom view of a sensor system, according to an embodiment.

As described above with respect to third adhesive portion 134, a connecting member can be coupled to a surface of a patient via one or more adhesive portions. FIGS. 5A-5C show variations of a system with examples of adhesive portions in various locations. FIG. 5A is a schematic illustration of a bottom view of a system 500. The system 500 can be the same or similar in structure and/or function to any of the systems described herein, such as the system 100 described with respect to FIG. 1. For example, the system 500 includes a first assembly 510, a second assembly 520, and a connecting member 530, which can be the same or similar in structure and/or function to the first assembly 110, the second assembly 120, and the connecting member 130, respectively. The connecting member 530 has a first end 536 coupled to the first assembly 510 and a second end 538 coupled to the second assembly 520. The connecting member 530 can be shaped as one period of a sinusoidal wave. For example, the connecting member 530 includes a first segment 537A, a second segment 537B, and a third segment 537C. The connecting member 530 also includes a first elastic hinge 539A and a second elastic hinge 539B. The first segment 537A is coupled to the second segment 537B via the first elastic hinge 539A. The second segment 537B is coupled to the third segment 537C via the second elastic hinge 539B. The first segment 537A, the second segment 537B, the third segment 537C, the first elastic hinge 539A, and the second elastic hinge 539B can collectively form a continuous and monolithic connecting member 530. The first assembly 510 and/or the second assembly 520 can be moved in one of the directions indicated by the double arrow L such that the connecting member 530 is stretched or compressed. The connecting member 530 includes an adhesive portion 534 distributed along the entire length of a bottom or skin-facing surface of the connecting member 530.

FIG. 5B is a schematic illustration of a bottom view of a system 500'. The system 500' can be the same or similar in structure and/or function to the system 500 shown in FIG. 5A, except that the system 500' includes a discrete adhesive portion 534' covering only a portion of the length of the bottom or skin-facing surface of a connecting member 530'. For example, the system 500' includes a first assembly 510', a second assembly 520', and the connecting member 530', which can be the same or similar in structure and/or function to the first assembly 510, the second assembly 520, and the connecting member 530, respectively. The connecting member 530' has a first end 536' coupled to the first assembly 510' and a second end 538' coupled to the second assembly 520'. The connecting member 530' includes a first segment 537A', a second segment 537B', and a third segment 537C'. The connecting member 530' also includes a first elastic hinge 539A' and a second elastic hinge 539B'. The first segment 537A' is coupled to the second segment 537B' via the first elastic hinge 539A'. The second segment 537B' is coupled to the third segment 537C' via the second elastic hinge 539B'. The connecting member 530' includes an adhesive portion 534' disposed on the second segment 537B'. Thus, the second segment 537B' can be coupled to a location on the surface of a patient via the adhesive portion 534', allowing for additional elasticity and reduced adhesive-skin contact area compared to if the connecting member 530 were coupled to the surface of the patient along the entire length of the connecting member 530.

FIG. 5C is a schematic illustration of a bottom view of a system 500″. The system 500″ can be the same or similar in structure and/or function to the system 500 shown in FIG. 5A, except that the system 500″ includes a first adhesive portion 534A″ and a second adhesive portion 534B″. For example, the system 500″ includes a first assembly 510″, a second assembly 520″, and a connecting member 530″, which can be the same or similar in structure and/or function to the first assembly 510, the second assembly 520, and the connecting member 530, respectively. The connecting member 530″ has a first end 536″ coupled to the first assembly 510″ and a second end 538″ coupled to the second assembly 520″. The connecting member 530″ includes a first segment 537A″, a second segment 537B″, and a third segment 537C″. The connecting member 530″ also includes a first elastic hinge 539A″ and a second elastic hinge 539B″. The first segment 537A″ is coupled to the second segment 537B″ via the first elastic hinge 539A″. The second segment 537B″ is coupled to the third segment 537C″ via the second elastic hinge 539B″. The connecting member 530″ includes a first adhesive portion 534A″ disposed on the first elastic hinge 539A″ (e.g., at a first nodal point of the connecting member 530″) and a second adhesive portion 534A″ disposed on the second elastic hinge 539B″ (e.g., at a second nodal point of the connecting member 530″). Thus, the first elastic hinge 539A″ and the second elastic hinge 539B″ can each be coupled to a location on the surface of a patient via the first adhesive portion 534A″ and the second adhesive portion 534B″, respectively, such that the skin deformation-induced stress is reduced at the skin adhesive-skin interface of each adhesive portion compared to if the connecting member 530″ were attached via only one adhesive portion.

Figure 6:
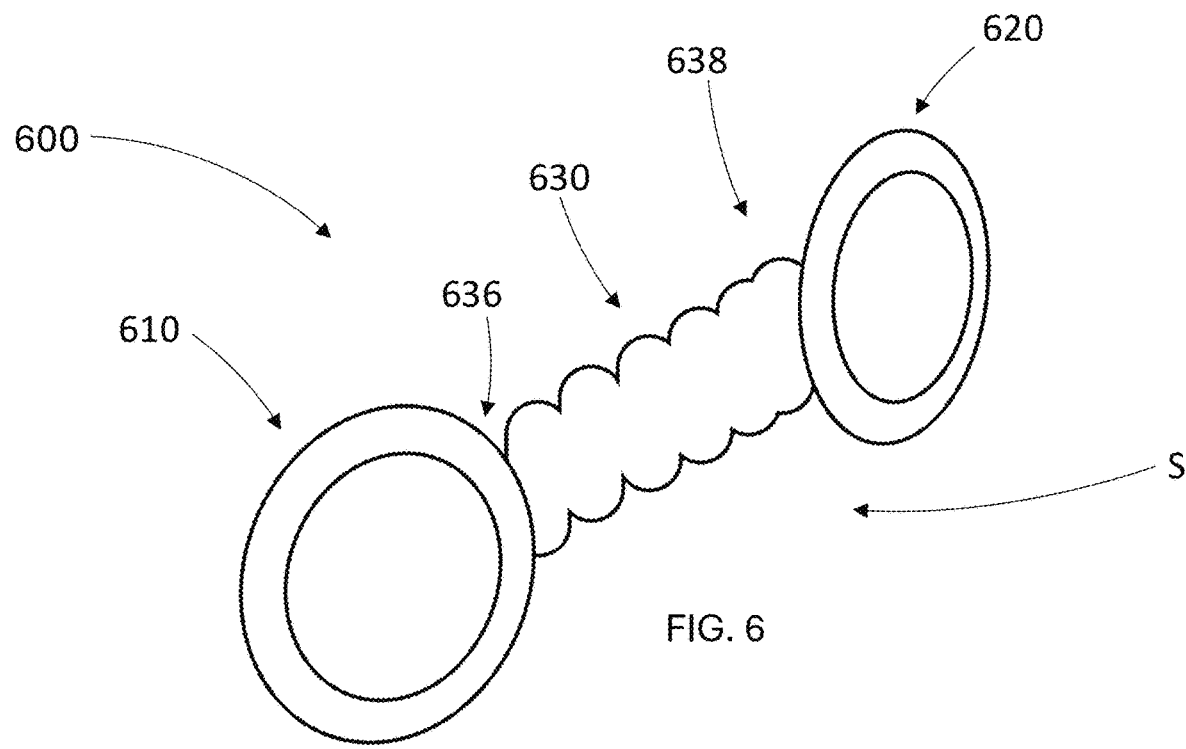
FIG. 6 is a perspective view of a sensor system, according to an embodiment.

In some implementations, the first assembly and the second assembly can be coupled to each other via a non-elastic, flexible connecting member. For example, FIG. 6 is a perspective view of a system 600 disposed on the surface S of a patient. The system 600 can be the same or similar in structure and/or function to any of the systems described herein, such as the system 100. For example, the system 600 includes a first assembly 610, a second assembly 620, and a connecting member 630, which can be the same or similar in structure and/or function to the first assembly 110, the second assembly 120, and the connecting member 130, respectively. The connecting member 630 has a first end 636 coupled to the first assembly 610 and a second end 638 coupled to the second assembly 620. The connecting member 630 can be non-elastic and flexible. The connecting member 630 can, for example, include a flexible strap. In some implementations, the connecting member 630 can be coupled to a surface of a patient via an adhesive portion. The adhesive portion can be disposed on a portion or all of a skin-contacting surface of the connecting member 630. Since the connecting member 630 is non-elastic, however, the system 600 cannot accommodate deformation (e.g., stretching) of the surface S. Rather, the system 600 will experience strain over the length of the system 600 and will apply the strain to the surface S, causing the skin-adhesive interface between each of the first assembly 610 and the second assembly 620 and the surface S will experience greater stress compared to if the connecting member 630 were elastic. Thus, the skin-adhesive interface between the system 600 and the surface S can experience adhesion loss due to the system 600 applying stress to the surface S via deformation of the surface S by the system 600.

Figure 7:
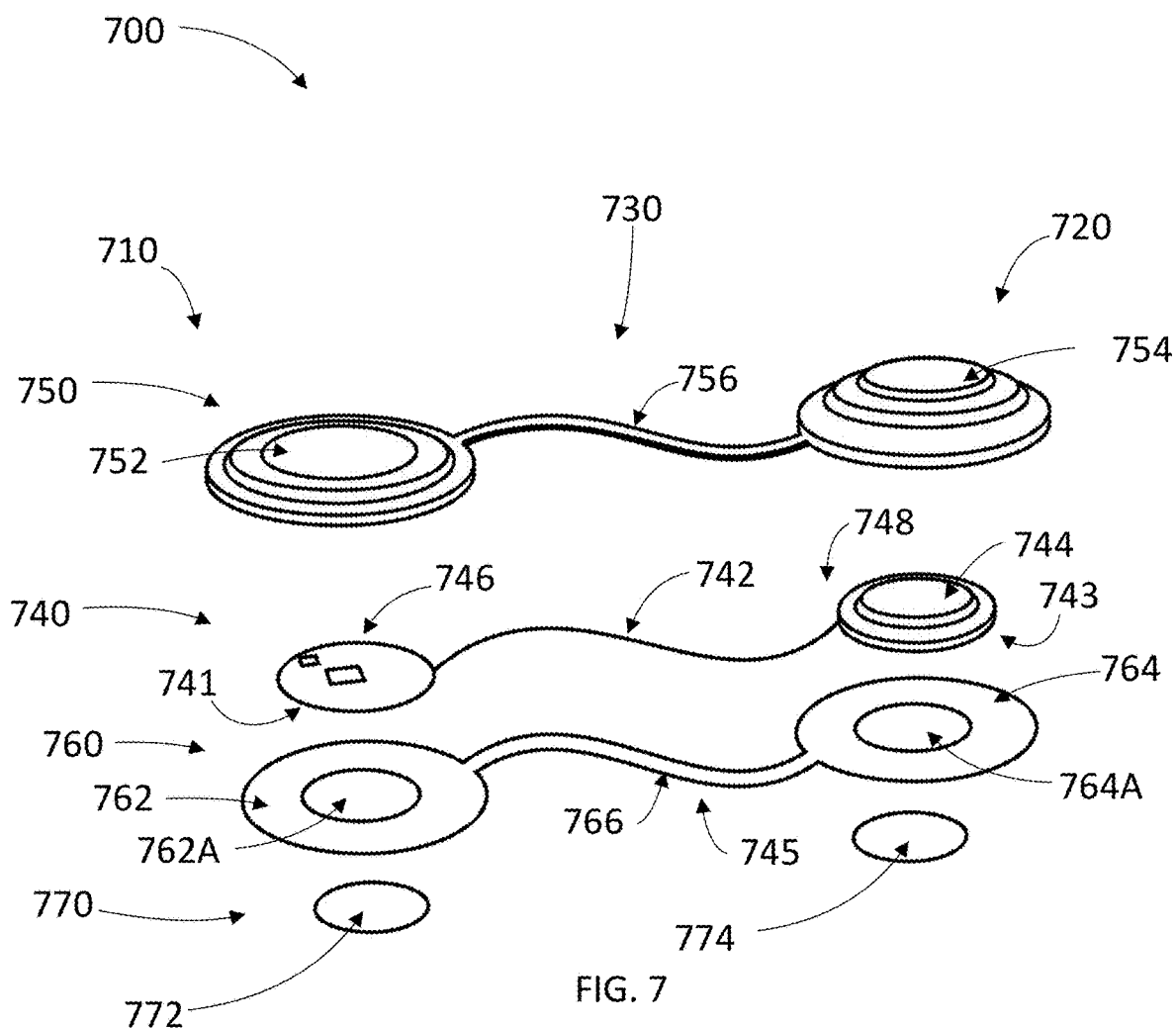
FIG. 7 is a perspective exploded view of a sensor system, according to an embodiment.

FIG. 7 is a perspective exploded view of a system 700. The system 700 can be the same or similar in structure and/or function to any of the systems described herein, such as, for example, the system 100. For example, the system 700 includes a first assembly 710, a second assembly 720, and a connecting member 730 that can be the same or similar in structure and/or function to the first assembly 110, the second assembly 120, and/or the connector 130, respectively. The first assembly 710 includes a first upper housing 752, a portion 746 of a composite assembly 740, a first lower housing 762, and a first adhesive portion (not shown). The portion 746 can include any suitable electronic components (e.g., a processor and a memory). The first lower housing 762 defines an opening 762A such that an electrode 741 disposed on a bottom side of the portion 746 is accessible through the opening 762A. The first assembly 710 also includes a hydrogel portion 772.

The second assembly 720 includes a second upper housing 754, a portion 744 of the composite assembly 740, a second lower housing 764, and a second adhesive portion (not shown). The portion 744 can include any suitable electronic components (e.g., an energy storage device such as a coin cell battery). The second lower housing 764 defines an opening 764A such that an electrode 743 disposed on a bottom side of the portion 744 is accessible through the opening 764A. The second assembly 720 also includes a hydrogel portion 774.

In some implementations, the composite assembly 740 includes a tab contact 748. The tab contact 748 can be integrally formed with the composite board of the composite assembly 740 and can be folded to contact the top of the energy storage device of the portion 744 as shown in FIG. 7. In some implementations, the energy storage device can be coupled to the composite board of the composite assembly 740 via a conductive adhesive. In some implementations, contacts of the energy storage device can be coupled to the composite board via spot welding.

The connecting member 730 includes a third upper housing 756, a portion 742 of the composite assembly 740, a third lower housing 766, and a third adhesive portion (not shown). The third lower housing 766 has a skin-facing surface 745 along the full length of the portion 742. The portion 742 can include a composite board including an insulator and at least one conductive trace (e.g., a flexible printed circuit board). The insulator can include, for example, polyimide. The at least one conductive trace can include, for example, copper. In some implementations, the composite board can include a polyimide with double-sided copper conductors. In some implementations, the portion 742 can include multiple layers (e.g., two, three, or more layers), each layer including at least one conductive trace. In some implementations, the portion 742 can include multiple layers including at least one conductive trace, each layer including at least one conductive trace coupled to another layer including at least one conductive trace via an insulative layer. The third adhesive portion can cover the entire skin-facing surface 745 of the third lower housing 766. In some implementations, the system 700 includes three conductive traces extending from the first assembly 710 to the second assembly 720. For example, a first conductive trace can extend from a positive side of the energy storage device of the portion 744 to the portion 746, a second conductive trace can extend from a negative side of the energy storage device of the portion 744 to the portion 746, and the third conductive trace can extend from the electrode 743 to the portion 746. Similarly as described above with reference to the connecting member 130, in some implementations the connecting member 730 (and/or the portion 742) may have a thickness equal to or less than 100 μm. In some implementations, the height of the connecting member 730 (and/or the portion 742) can be, for example, equal to or less than 36 μm. In some implementations, the spring constant of the connecting member 730 (and/or the portion 742) (in the X-direction) can increase proportionally to a cube of the thickness of the connecting member 730 (and/or the portion 742) and linearly with respect to the height of the connecting member 730 (and/or the portion 742).

As shown in FIG. 7, the first upper housing 752, the second upper housing 754, and the third upper housing 756 can collectively form a cover layer 750. The first lower housing 762, the second lower housing 764, and the third lower housing 766 can collectively form a bottom layer 760. The bottom layer 760 can be coupleable to a surface of a skin via the first adhesive portion, the second adhesive portion, and/or the third adhesive portion such that the bottom layer 760 secures the composite assembly 740 to the surface of the skin. In some implementations, the cover layer 750 (including the first upper housing 752, the second upper housing 754, and the third upper housing 756) can be monolithically or integrally formed. In some implementations, the bottom layer 760 (including the first lower housing 762, the second lower housing 764, and the third lower housing 766) can be monolithically or integrally formed.

Figure 8A:
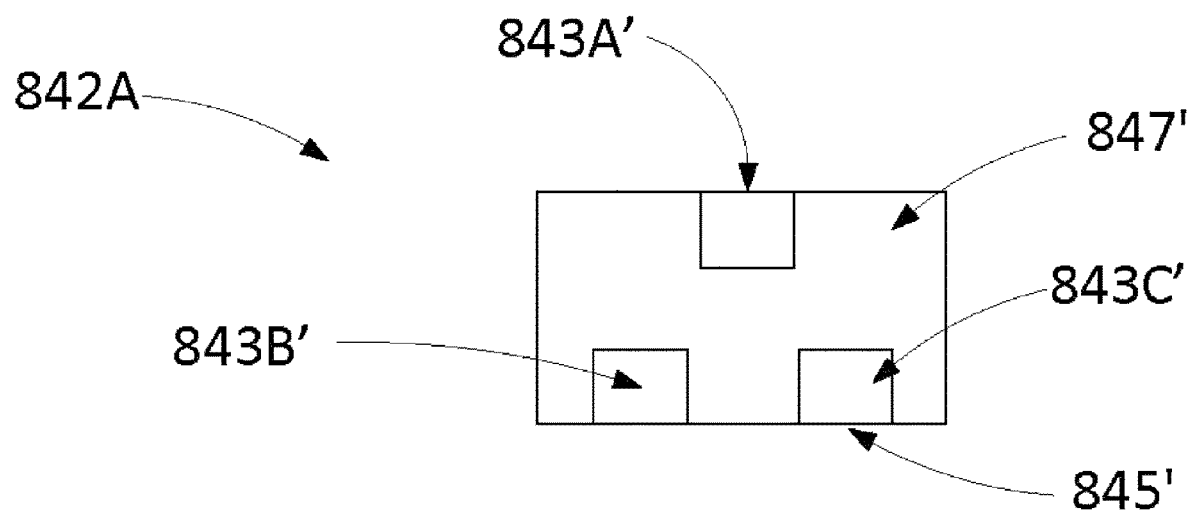
FIG. 8A is a schematic illustration of a cross section of a connecting member of a sensor system, according to an embodiment.

FIGS. 8A-8D illustrate various example arrangements of conductive traces within a connecting member. FIG. 8A is a cross-sectional schematic illustration of a portion 842A of a composite assembly, which can be the same or similar in structure and/or function to the composite assembly 740 described above with reference to FIG. 7. The portion 842A includes an insulative portion 847' and a first conductive trace 843A', a second conductive trace 843B', and a third conductive trace 843C' disposed within the insulative portion 847'. For example, the first conductive trace 843A', the second conductive trace 843B', and the third conductive trace 843C' can be etched into or printed on the insulative portion 847'. The portion 842A has a skin-facing surface 845'. The first conductive trace 843A', the second conductive trace 843B', and the third conductive trace 843C' can be disposed at varying locations relative to the skin-facing surface 845' such that at least one of the first conductive trace 843A', the second conductive trace 843B', and the third conductive trace 843C' is disposed farther from the skin-facing surface 845'. Thus, at least some of the conductive traces of the portion 842A can be vertically-arranged relative to other conductive traces such that the portion 842A can be narrower (i.e., have reduced thickness in an X-Y plane parallel to the surface of the patient) and more elastic than if the portion 842A included only horizontally-distributed conductive traces. Although not shown, the portion 842A can include any suitable number of vias electrically coupling a conductive trace to another conductive trace in any suitable arrangement.

Figure 8B:
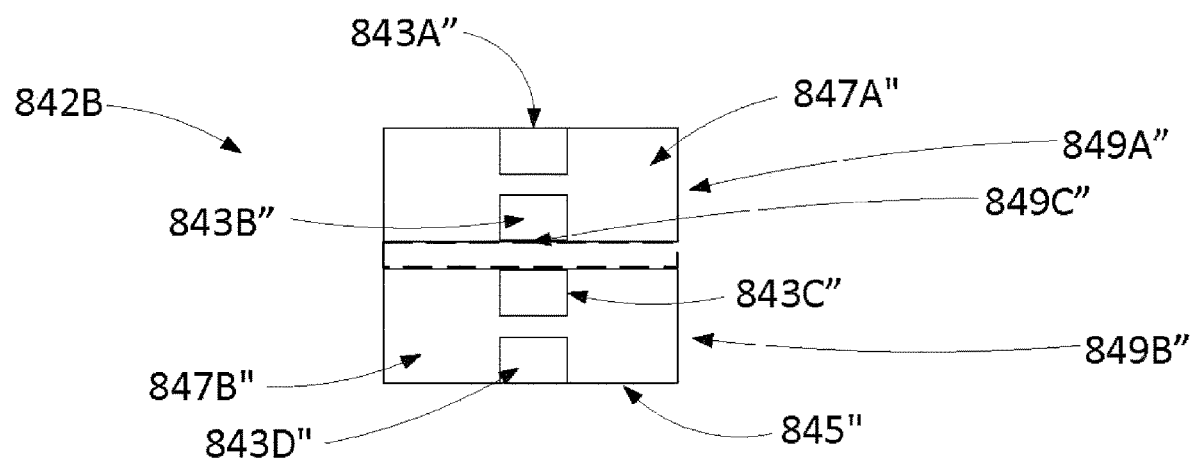
FIG. 8B is a schematic illustration of a cross section of a connecting member of a sensor system, according to an embodiment.

FIG. 8B is a cross-sectional schematic illustration of a portion 842B of a composite assembly, which can be the same or similar in structure and/or function to the composite assembly 740 described above with reference to FIG. 7. The portion 842B is a multi-layer composite board, including a first layer 849A" and a second layer 849B". The first layer 849A" includes an insulative portion 847A", a first conductive trace 843A", and a second conductive trace 843B". The first conductive trace 843A" and the second conductive trace 843B" can be etched into or printed on the first layer 849A". The second layer 849B" includes an insulative portion 847B", a third conductive trace 843C", and a fourth conductive trace 843D". The third conductive trace 843C" and the fourth conductive trace 843D" can be etched into or printed on the second layer 849B". The second layer 849B" has a skin-facing surface 845". The portion 842B can include an insulative layer 849C" disposed between the first layer 849A" and the second layer 894B". The first layer 849A" can be stacked relative to the second layer 849B" such that the first conductive trace 843A" is disposed farther from the skin-facing surface 845" than the second conductive trace 843B". Although each of the first layer 849A" and the second layer 849B" are shown as including two conductive traces, the first layer 849A" and the second layer 849B" can each include any suitable number of conductive traces (e.g., one, three, four, or more). Furthermore, although the portion 842B is shown as having only two layers including conductive traces, the portion 842B can have any suitable number of layers of conductive traces (e.g., three layers, four layer, or more). Each of the layers including conductive traces can be separated by an insulative layer similar to insulative layer 849C". Thus, portion 842B can include vertically-stacked layers each including at least one conductive trace such that the portion 842B can be narrower and more elastic than if the portion 842B included horizontally-distributed conductive traces.

Figure 8C:
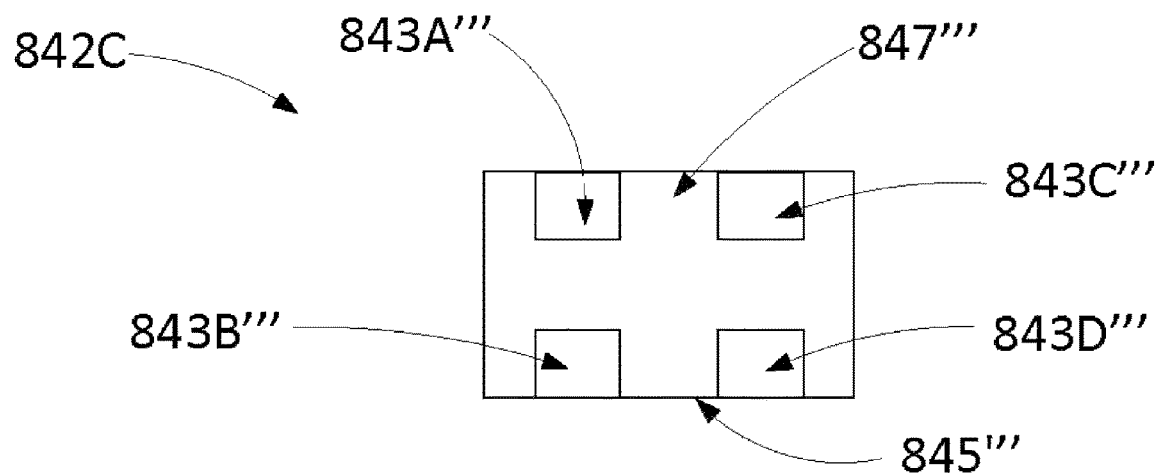
FIG. 8C is a schematic illustration of a cross section of a connecting member of a sensor system, according to an embodiment.

FIG. 8C is a cross-sectional schematic illustration of a portion 842C of a composite assembly, which can be the same or similar in structure and/or function to the composite assembly 740 described above with reference to FIG. 7. The portion 842C includes an insulative portion 847''' and a first conductive trace 843A''', a second conductive trace 843B''', a third conductive trace 843C''', and a fourth conductive trace 843D''' disposed within or coupled to the insulative portion 847'''. For example, the first conductive trace 843A''' and the third conductive trace 843C''' can be etched into or printed on a first layer of the insulative portion 847''' and the second conductive trace 843B''' and the fourth conductive trace 843D''' can be etched into or printed on a second layer of the insulative portion 847'''. The portion 842C has a skin-facing surface 845'''. The first layer is stacked on top of the second layer such that the first conductive trace 843A''' and the third conductive trace 843C''' are disposed farther from the skin-facing surface 845''' than the second conductive trace 843B''' and the fourth conductive trace 843D'''. By disposing at least some of the conductive traces (e.g., 843A''' and 843C''') above others of the conductive traces (e.g., 843B''' and 843D'''), the portion 842C can be narrower and more elastic compared to if the conductive traces were horizontally distributed.

Figure 8D:
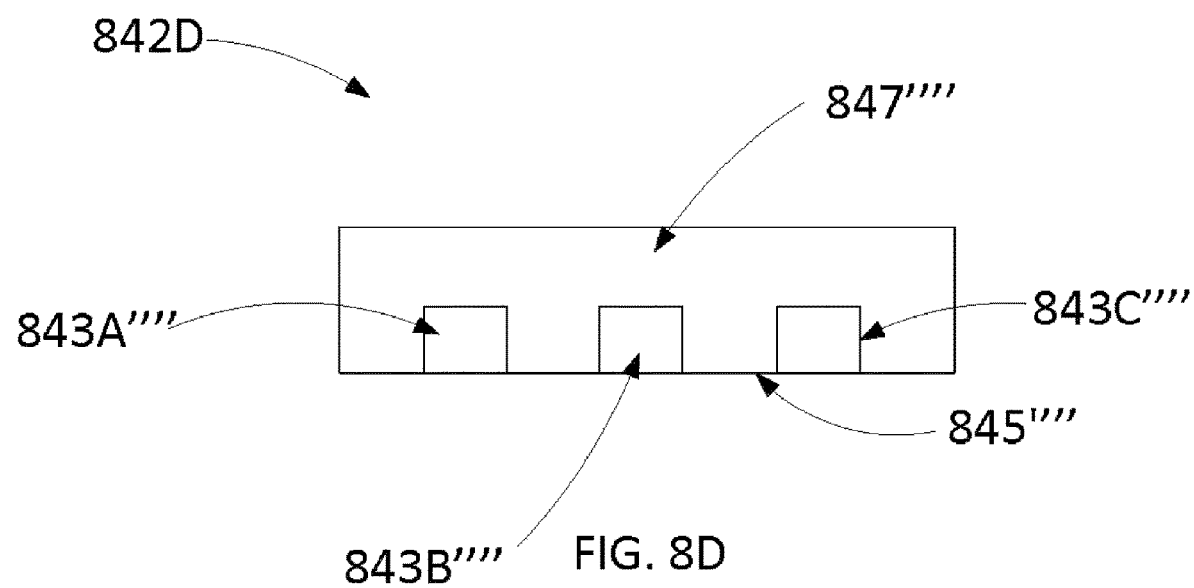
FIG. 8D is a schematic illustration of a cross section of a connecting member of a sensor system, according to an embodiment.

FIG. 8D is a cross-sectional schematic illustration of a portion 842D of a composite assembly, which can be the same or similar in structure and/or function to the composite assembly 740 described above with reference to FIG. 7. The portion 842D includes an insulative portion 847'''' and a first conductive trace 843A'''', a second conductive trace 843B'''', and a third conductive trace 843C'''' disposed within or coupled to the insulative portion 847''''. For example, the first conductive trace 843A'''', the second conductive trace 843B'''', and the third conductive trace 843C'''' can be etched into or printed on the insulative portion 847''''. The first conductive trace 843A'''', the second conductive trace 843B'''', and the third conductive trace 843C'''' are horizontally distributed (i.e., disposed in parallel to one another within a plane that is disposed parallel to a skin-facing surface 845' of the portion 842D). Although the first conductive trace 843A'''', the second conductive trace 843B'''', and the third conductive trace 843C'''' are shown as being disposed on the skin-facing surface 845'''' of the portion 842D, the first conductive trace 843A'''', the second conductive trace 843B'''', and the third conductive trace 843C' can be disposed on any suitable side or on any suitable layer of the portion 842D.

Figure 9:
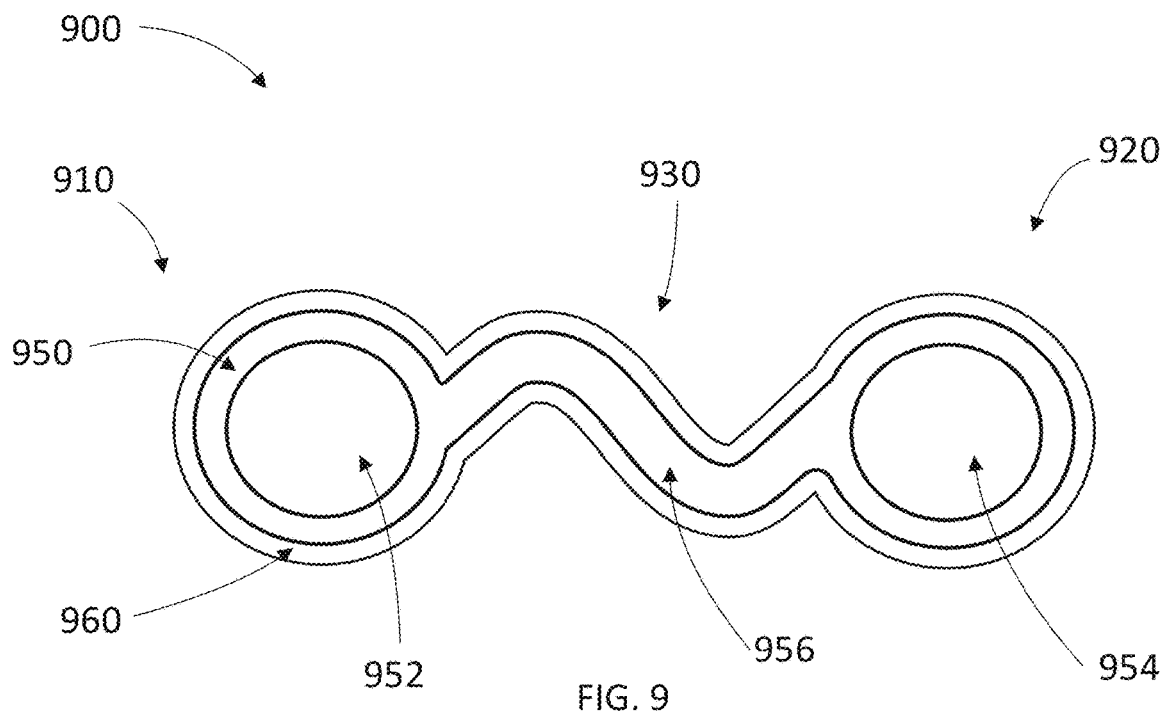
FIG. 9 is a top view of a sensor system, according to an embodiment.

FIG. 9 is a top view of a system 900. The system 900 can be the same or similar in structure and/or function to any of the systems described herein such as, for example, the system 100 or the system 700. For example, the system 900 includes a first assembly 910, a second assembly 920, and a connecting member 930 that can be the same or similar in structure and/or function to the first assembly 710, the second assembly 720, and the connecting member 730, respectively. The system 900 includes a cover layer 950 and an adhesive layer 960. The cover layer 950 includes a first housing 952, a second housing 954, and a third housing 956.

Figure 10:
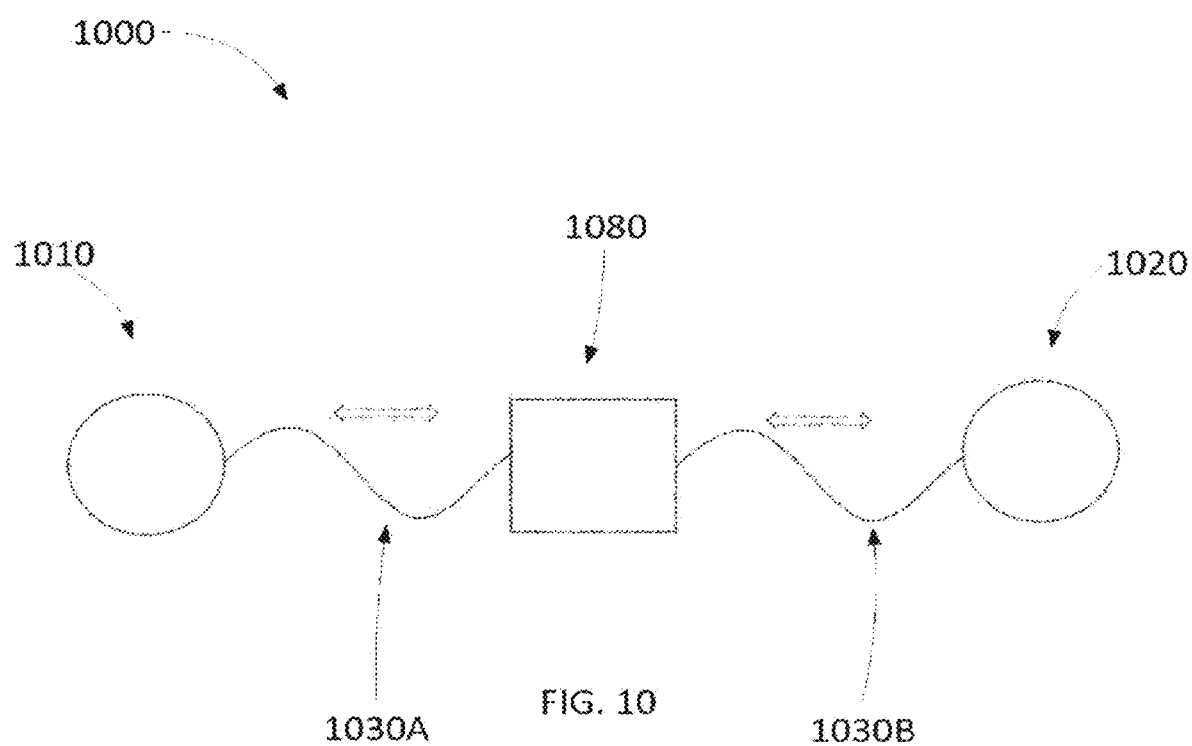
FIG. 10 is a schematic illustration of a sensor system, according to an embodiment.

In some embodiments, a system can include an additional assembly. For example, FIG. 10 is a schematic illustration of a system 1000. The system 1000 includes a first assembly 1010, a second assembly 1020, and a third assembly 1080. The first assembly 1010 can be coupled to the third assembly 1080 via a first connecting member 1030A and the second assembly 1020 can be coupled to the third assembly 1080 via a second connecting member 1030B. The system 1000 can be similar in structure and/or function to any of the systems described herein. For example, the first assembly 1010 and the second assembly 1020 can be the same or similar in structure and/or function to the first assembly 110 and/or the second assembly 120. The first connecting member 1030A and the second connecting member 1030B can each be the same or similar to any of the connecting members described herein, such as, for example, the connecting member 130.

The third assembly 1080 can be the same or similar in structure and/or function to any of the assemblies described herein, such as, for example, the first assembly 110 and/or the second assembly 120. The third assembly 1080 can include a portion of a composite assembly similar to the composite assembly 140. For example, electronic components of the composite assembly (e.g., the processor and/or the battery) can be included in the third assembly 1080. In some implementations, the third assembly 1080 includes a housing portion. In some implementations, the third assembly 1080 includes an adhesive portion (not shown) configured to couple the third assembly 1080 to a surface of a patient. In some implementations, the third assembly 1080 includes an electrode (not shown) configured to be coupled to the surface of the patient.

In some implementations, the first assembly 1010 can include a first electrode and the second assembly 1020 can include a second electrode. The third assembly 1080 can include the processor and the battery. The first electrode and the second electrode can be separately optimized for electrode performance. For example, the first electrode and the second electrode can be made soft and compact in size since the first electrode and the second electrode are not within the same housing as the electronic components (e.g., the processor and/or the battery) of the third assembly 1080. Thus, each of the first electrode and the second electrode can be conformal electrodes. For example, in some implementations, each of the first assembly 1010 and the second assembly 1020 can include a backing layer of thermoplastic polyurethane (TPU) on which silver/silver chloride (Ag/AgCl) can be printed. A skin adhesive layer can be disposed on a skin-facing surface of the backing and can define an opening surrounding a portion of the Ag/AgCl (e.g., an opening having a diameter of about 10 mm). The skin adhesive layer can include, for example, a soft, pliable polyurethane film having a thin acrylic absorbent adhesive (e.g., MED 5577A manufactured by Avery Dennison Corporation). A hydrogel pillow having a diameter smaller than the diameter of the opening of the skin adhesive layer (e.g., a diameter of about 6 mm) can be disposed within the opening defined by the skin adhesive in contact with the skin-facing surface of the backing and the printed Ag/AgCl electrode. The hydrogel pillow can be, for example, AG625 Sensing Gel manufactured by Axelgaard Manufacturing Co., Ltd.

Figure 11:
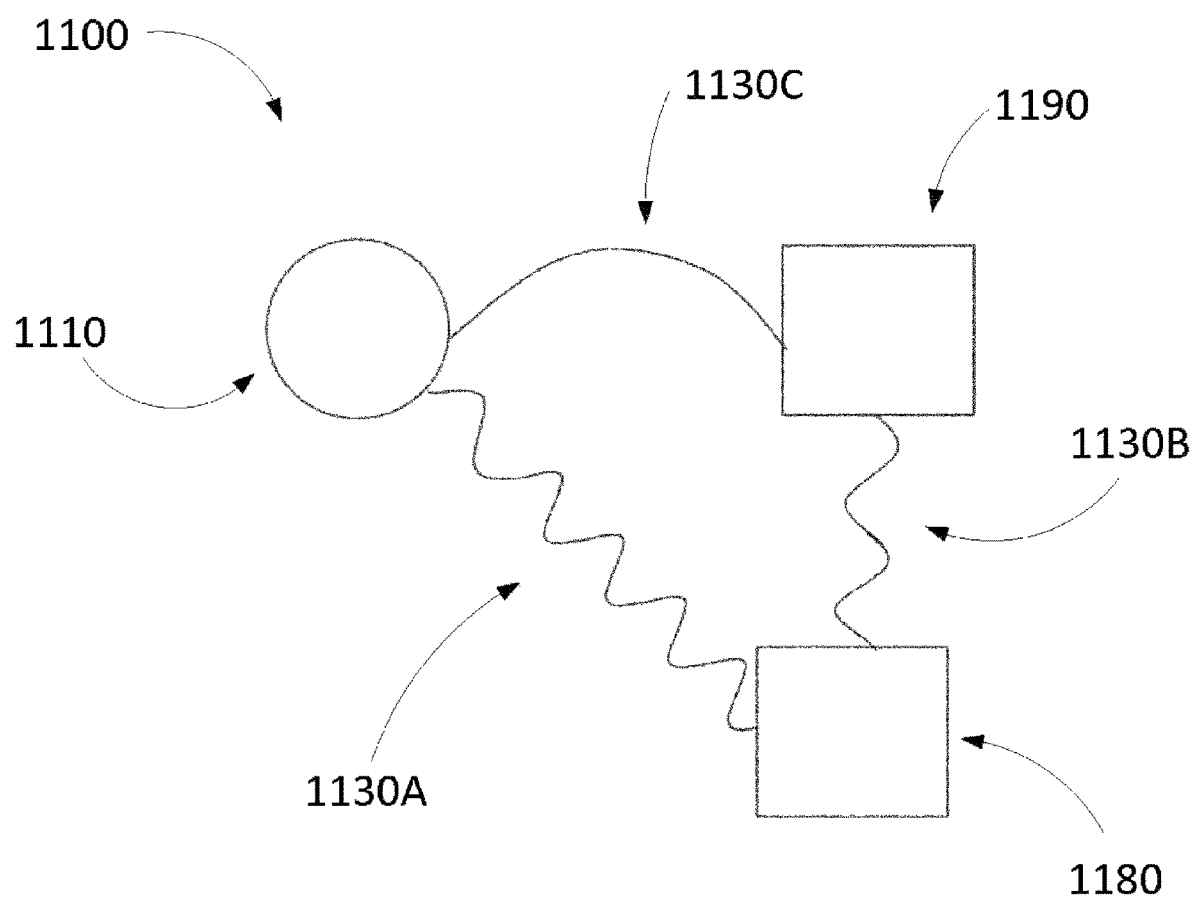
FIG. 11 is a schematic illustration of a sensor system, according to an embodiment.

FIG. 11 is a schematic illustration of a system 1100. The system 1100 includes a first assembly 1110, a second assembly 1180, and a third assembly 1190. The first assembly 1110, the second assembly 1180, and/or the third assembly 1190 can be arranged in any suitable configuration on the surface of a patient. The first assembly 1110 can be coupled to the second assembly 1180 via a first connecting member 1130A. The second assembly 1180 can be coupled to the third assembly 1190 via a second connecting member 1130B. The first assembly 1110 can be coupled to the third assembly 1190 via a third connecting member 1130C. The system 1100 can be similar in structure and/or function to any of the systems described herein. For example, the first assembly 1110, the second assembly 1180, and/or the third assembly 1190 can be the same or similar in structure and/or function to the first assembly 110 and/or the second assembly 120 described above with respect to the system 100. The first connecting member 1130A, the second connecting member 1130B, and/or the third connecting member 1130C can each be the same or similar to any of the connecting members described herein, such as, for example, the connecting member 130. For example, the first connecting member 1130A can be shaped as a sinusoidal wave including five periods. The second connecting member 1130B can be shaped as a sinusoidal wave including two periods. The third connecting member 1130C can be shaped as an arch.

The second assembly 1180 and/or the third assembly 1190 can include a portion of a composite assembly similar to composite assembly 140. For example, electronic components of the composite assembly can be included in the second assembly 1180 and/or the third assembly 1190. In some implementations, the second assembly 1180 and/or the third assembly 1190 includes a housing portion. In some implementations, the second assembly 1180 and/or the third assembly 1190 includes an adhesive portion (not shown) configured to couple the second assembly 1180 and/or the third assembly 1190 to a surface of a patient. In some implementations, the second assembly 1180 and/or the third assembly 1190 includes an electrode (not shown) configured to be coupled to the surface of the patient.

Figure 12:
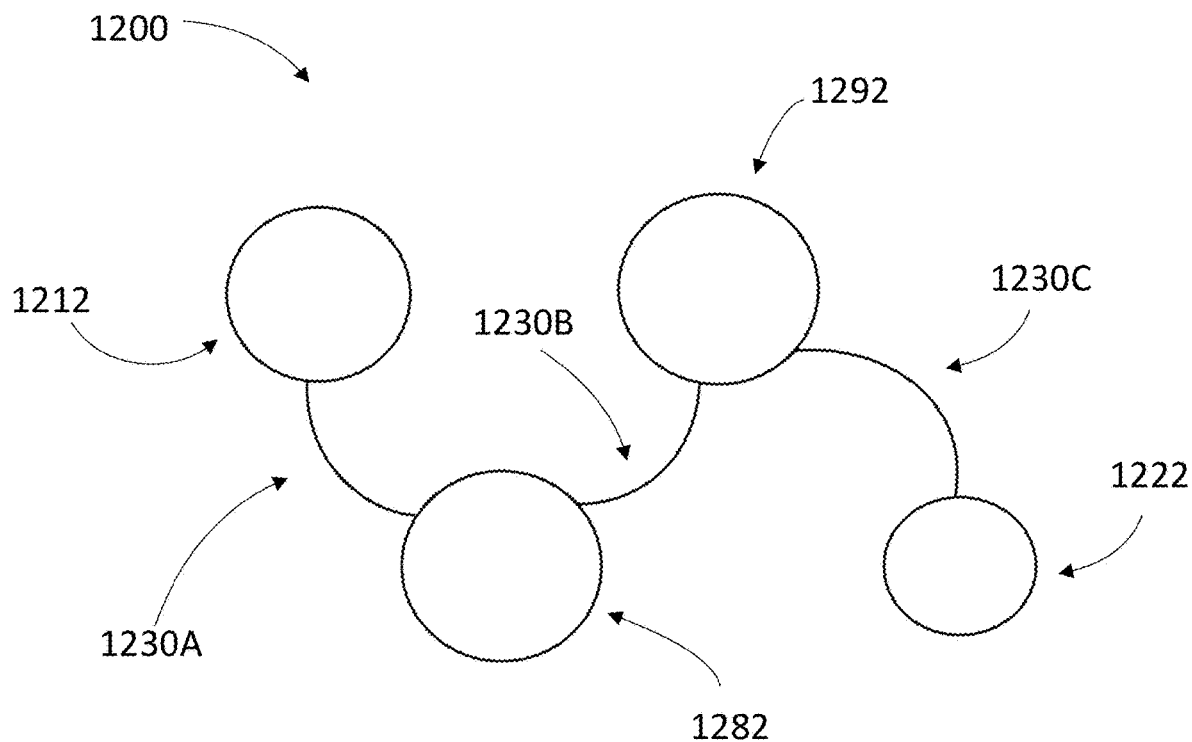
FIG. 12 is a schematic illustration of a sensor system, according to an embodiment.

FIG. 12 is a schematic illustration of a system 1200. The system 1200 can be similar in structure and/or function to any of the systems described herein. The system 1200 includes a first electrode 1212, a second electrode 1222, an energy storage device 1282, and an electronics module 1292. The first electrode 1212 can be coupled to the energy storage device 1282 via a first connecting member 1230A. The energy storage device 1282 can be coupled to the electronics module 1292 via a second connecting member 1230B. The electronics module 1292 can be coupled to the second electrode 1222 via a third connecting member 1230C. The first connecting member 1230A, the second connecting member 1230B, and/or the third connecting member 1230C can each be the same or similar in structure and/or function to any of the connecting members described herein. In some implementations, the first electrode 1212, the second electrode 1222, the energy storage device 1282, and the electronics module 1292 each include an adhesive portion (not shown) configured to couple the first electrode 1212, the second electrode 1222, the energy storage device 1282, and the electronics module 1292 to a surface of a patient. The system 1200 can include a cover portion or a number of discrete cover portions (e.g., housings) shaped and sized to cover some or all of the first electrode 1212, the second electrode 1222, the energy storage device 1282, the electronics module 1292, the first connecting member 1230A, the second connecting member 1230B, and/or the third connecting member 1230C. The first electrode 1212 and the second electrode 1222 can be the same or similar in structure and/or function to the first electrode and second electrode or first assembly 1010 and second assembly 1020 described with respect to the system 1000.

The first electrode 1212, the second electrode 1222, the energy storage device 1282, and the electronics module 1292 can be arranged in any suitable configuration on the surface of the patient. The electronics module 1292 can include any of the electrical components of a composite assembly similar to the composite assembly 140 described above. Each of the first electrode 1212 and the second electrode 1222 can be separately optimized for electrode performance. For example, the first electrode 1212 and the second electrode 1222 can be made soft and compact in size since the first electrode 1212 and the second electrode 1222 are not directly coupled to and/or are in separate housings as the electronic components of the electronics module 1292 or the energy storage device 1282. The electronics module 1292 can be separately optimized due to not being directly coupled to and/or not within the same housing as the first electrode 1212 and the second electrode 1222. For example, the energy storage device 1282 and/or the electronics module 1292 can be increased in size while keeping the first electrode 1212 and the second electrode 1222 small.

Figure 13:
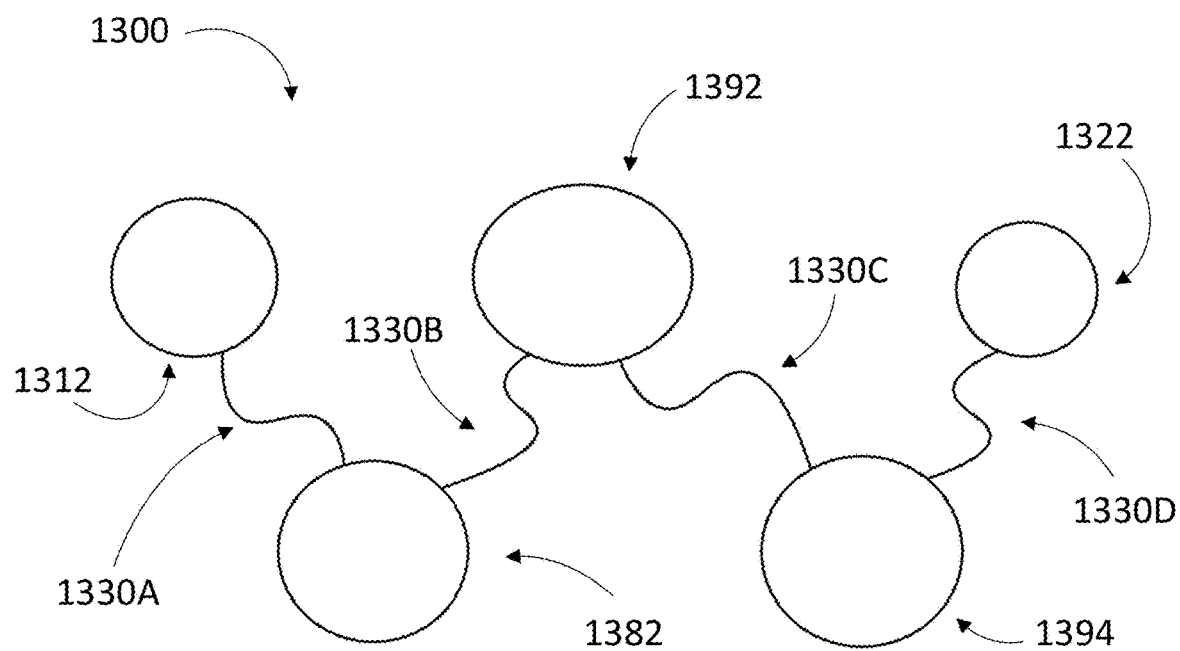
FIG. 13 is a schematic illustration of a sensor system, according to an embodiment.

In some implementations, rather than including one electronics module, a system can include two or more separate electronics modules. For example, FIG. 13 is a schematic illustration of a system 1300. The system 1300 can be similar in structure and/or function to any of the systems described herein. The system 1300 includes a first electrode 1312, a second electrode 1322, an energy storage device 1382, a first electronics module 1392, and a second electronics module 1394. The first electrode 1312 can be coupled to the energy storage device 1382 via a first connecting member 1330A. The energy storage device 1382 can be coupled to the first electronics module 1392 via a second connecting member 1330B. The first electronics module 1392 can be coupled to the second electronics module 1394 via a third connecting member 1330C. The second electronics module 1394 can be coupled to the second electrode 1322 via a fourth connecting member 1330D. The first connecting member 1330A, the second connecting member 1330B, the third connecting member 1330C, and/or the fourth connecting member 1330D can each be the same or similar in structure and/or function to any of the connecting members described herein. In some implementations, the first electrode 1312, the second electrode 1322, the energy storage device 1382, the first electronics module 1392 and the second electronics module 1394 each include an adhesive portion (not shown) configured to couple the first electrode 1312, the second electrode 1322, the energy storage device 1382, the first electronics module 1392, and the second electronics module 1394 to a surface of a patient. The system 1300 can include a cover portion or a number of discrete cover portions (e.g., housings) shaped and sized to cover some or all of the first electrode 1312, the second electrode 1322, the energy storage device 1382, the first electronics module 1392, the second electronics module 1394, the first connecting member 1330A, the second connecting member 1330B, the third connecting member 1330C, and/or the fourth connecting member 1330D. The first electrode 1312 and the second electrode 1322 can be the same or similar in structure and/or function to the first electrode and second electrode or first assembly 1010 and second assembly 1020 described with respect to the system 1000.

The first electrode 1312, the second electrode 1322, the energy storage device 1382, the first electronics module 1392, and the second electronics module 1394 can be arranged in any suitable configuration on the surface of the patient. The first electronics module 1392 and the second electronics module 1394 can include any of the electrical components of a composite assembly similar to the composite assembly 140 described above. Each of the first electrode 1312 and the second electrode 1322 can be separately optimized for electrode performance. For example, the first electrode 1312 and the second electrode 1322 can be made soft and compact in size since the first electrode 1312 and the second electrode 1322 are not directly coupled to and/or not within the same housing as the electronic components of the first electronics module 1392, the second electronics module 1394, or the energy storage device 1382. The first electronics module 1392 and/or the second electronics module 1394 can be separately optimized due to not being directly coupled to and/or not within the same housing as each other or the first electrode 1312 and the second electrode 1322. For example, the energy storage device 1382, the first electronics module 1392, and/or the second electronics module 1394 can have a size (e.g., perimeter) greater than the perimeter of the electrodes while the first electrode 1312 and the second electrode 1322 can have a smaller size (e.g., perimeter) than the energy storage device 1382, the first electronics module 1392, and/or the second electronics module 1394. As shown in FIG. 13, the system 1300 can be arranged in a zig-zag pattern such that the system 1300 has elasticity.

Figure 14A:
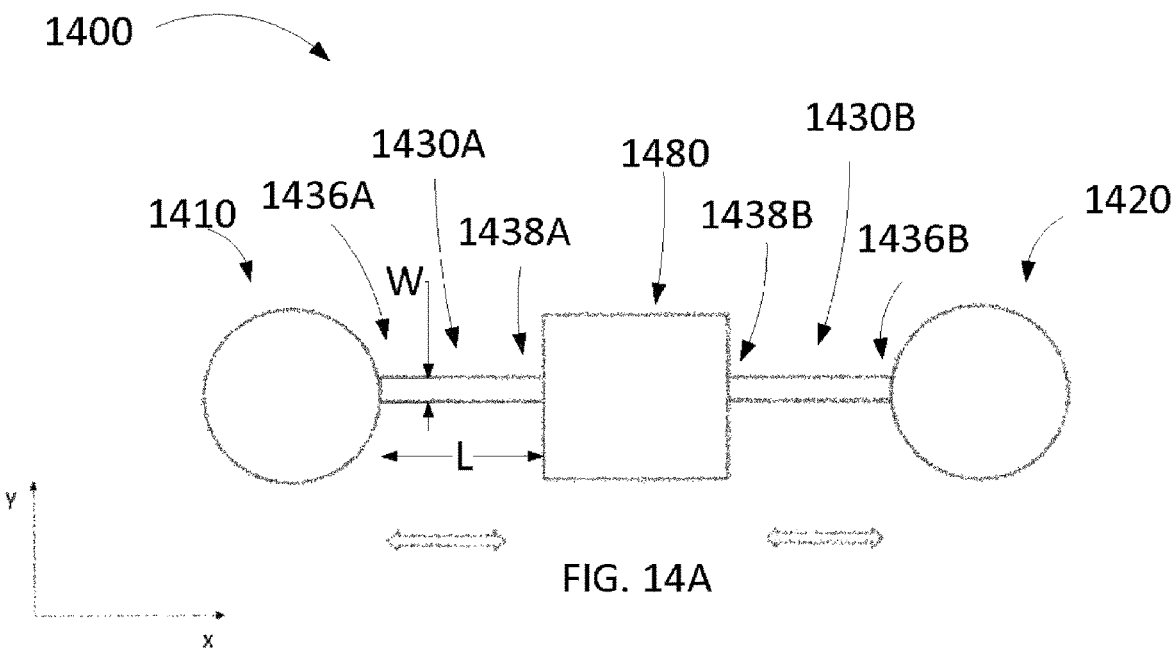
FIG. 14A is an illustration of a top view of a sensor system, according to an embodiment.
Figure 14B:
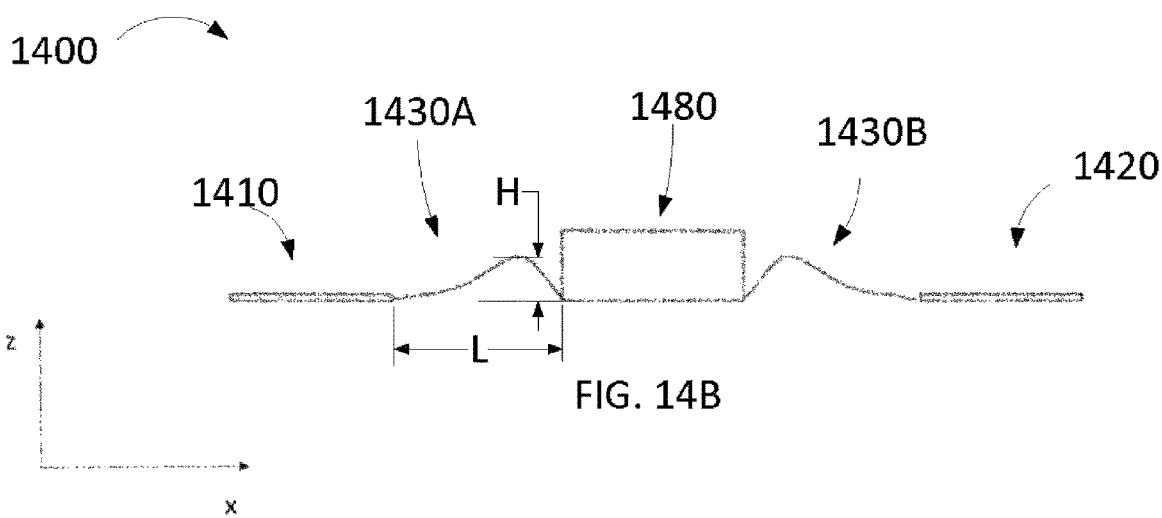
FIG. 14B is an illustration of a side view of the sensor system of FIG. 14A.

In some embodiments, a system can include connecting members that are configured to transition among various heights relative to the surface of the patient. For example, FIGS. 14A and 14B are schematic illustrations of a top view and a side view, respectively, of a system 1400. The system 1400 includes a first assembly 1410, a second assembly 1420, and a third assembly 1480. The first assembly 1410 can be coupled to the third assembly 1480 via a first connecting member 1430A and the second assembly 1420 can be coupled to the third assembly 1480 via a second connecting member 1430B. The system 1400 can be similar in structure and/or function to any of the systems described herein. For example, the first assembly 1410 and the second assembly 1420 can be the same or similar in structure and/or function to the first assembly 110 and/or the second assembly 120. The first connecting member 1430A and the second connecting member 1430B can each be the same or similar to any of the connecting members described herein, such as, for example, the connecting member 130.

The third assembly 1480 can be the same or similar in structure and/or function to any of the assemblies described herein, such as, for example, the first assembly 110 and/or the second assembly 120. The third assembly 1480 can include a portion of a composite assembly similar to the composite assembly 140. For example, electronic components of the composite assembly (e.g., the processor and/or the battery) can be included in the third assembly 1480. In some implementations, the third assembly 1480 includes a housing portion. In some implementations, the third assembly 1480 includes an adhesive portion (not shown) configured to couple the third assembly 1480 to a surface of a patient. In some implementations, the third assembly 1480 includes an electrode (not shown) configured to be coupled to the surface of the patient.

The first connecting member 1430A has a first end 1436A coupled to the first assembly 1410 and a second end 1438A coupled to the third assembly 1480. The second connecting member 1430B has a first end 1436B coupled to the second assembly 1420 and a second end 1438B coupled to the third assembly 1480. In some implementations, the first connecting member 1430A and the second connecting member 1430B can each be sufficiently flexible such that the first connecting member 1430A and the second connecting member 1430B can change in shape or deform from an initial configuration or shape while remaining coupled to the third assembly 1480 and the first assembly 1410 or the second assembly 1420, respectively (e.g., due to movement of the skin locations to which the first assembly 1410, the second assembly 1420, and/or the third assembly 1480 are coupled). Thus, the first connecting member 1430A and the second connecting member 1430B can accommodate skin deformations by reducing stress at the skin-adhesive interface compared to a connecting member with an undeforming shape, causing better adhesion durability and better wear comfort for the user. In some implementations, each of the first connecting member 1430A and the second connecting member 1430B (e.g., one or more composite boards of the composite assembly) can be sufficiently elastic such that the first connecting member 1430A and/or the second connecting member 1430B can function as a spring arranged between the third assembly 1480 and the first assembly 110 or the third assembly 1480 and the second assembly 120, respectively, allowing for expansion and contraction of the length of the first connecting member 1430A and/or the second connecting member 1430B relative to an equilibrium or undeformed length.

The first connecting member 1430A and the second connecting member 1430B each have an overall length (e.g., a distance from the first end 1436A to the second end 1438A and a distance from the first end 1436B to the second end 1438B, respectively), an overall width (e.g., a distance from an outermost edge of each connecting member 1430A and 1430B extending in a first direction extending perpendicularly relative to a line extending between the first assembly 1410 and the third assembly 1480 or a line extending between the third assembly 1480 and the second assembly 1420, respectively, to an outermost edge of each connecting member 1430A and 1430B extending in a second direction opposite the first direction), and an overall height (e.g., a vertical distance from a portion of each connecting member 1430A and 1430B closest to a surface of a patient to a portion farthest from the surface of the patient when the system 1400 is coupled to the surface). The length of each connecting member 1430A and 1430B may be measured in an X-direction, the width of each connecting member 1430A and 1430B may be measured in a Y-direction perpendicular to the X-direction, and the height of each connecting member 1430A and 1430B may be measured in a Z-direction perpendicular to the X-direction and the Y-direction. For example, as shown in FIGS. 14A and 14B, the first connecting member 1430A has a length L, a width W, and a height H. Each connecting member 1430A and 1430B can have a first overall length, a first overall width, and a first overall height in the first configuration and a second overall length, a second overall width, and a second overall height in the second configuration. The first width and the second width can be equal. When the first assembly 1410 and the third assembly 1480 are closer to each other in the second configuration than the first configuration, the second length may be smaller than the first length and the second height may be greater than the first height. When the first assembly 1410 and the third assembly 1480 are farther from each other in the second configuration than in the first configuration, the second length may be greater than the first length and the second height may be smaller than the first height. Similarly, when the second assembly 1420 and the third assembly 1480 are closer to each other in the second configuration than the first configuration, the second length may be smaller than the first length and the second height may be greater than the first height. When the second assembly 1420 and the third assembly 1480 are farther from each other in the second configuration than in the first configuration, the second length may be greater than the first length and the second height may be smaller than the first height.

As shown in FIG. 14B, in some implementations, the first connecting member 1430A and the second connecting member 1430B can each include an arched or curved shape. For example, in some implementations, the first connecting member 1430A and the second connecting member 1430B can each include an arched or curved shape in an initial or undeformed configuration. In some implementations, the first connecting member 1430A and the second connecting member 1430B can each be straight in an initial or undeformed configuration and can include an arched or curved shape in a contracted configuration. In some implementations, the more contracted the first connecting member 1430A and the second connecting member 1430B become, the smaller the frequency and/or the larger the amplitude of the arch or curve of each of the first connecting member 1430A and the second connecting member 1430B. In some implementations, the first connecting member 1430A can include an arched or curved shape extending from the first end 1436A to the second end 1438A (e.g., closer to the second end 1438A than the first end 1436A) and the second connecting member 1430B can include an arched or curved shape extending from the first end 1436B to the second end 1438B (e.g., closer to the second end 1438B than the first end 1436B). As shown in FIG. 14B, each of the first connecting member 1430A and the second connecting member 1430B can be shaped and attached to the third assembly 1480 such that the arched or curved shape is outside of the third assembly 1480 (e.g., the second end 1438A and the second end 1438B are outside a housing of the third assembly 1480).

Figure 15A:
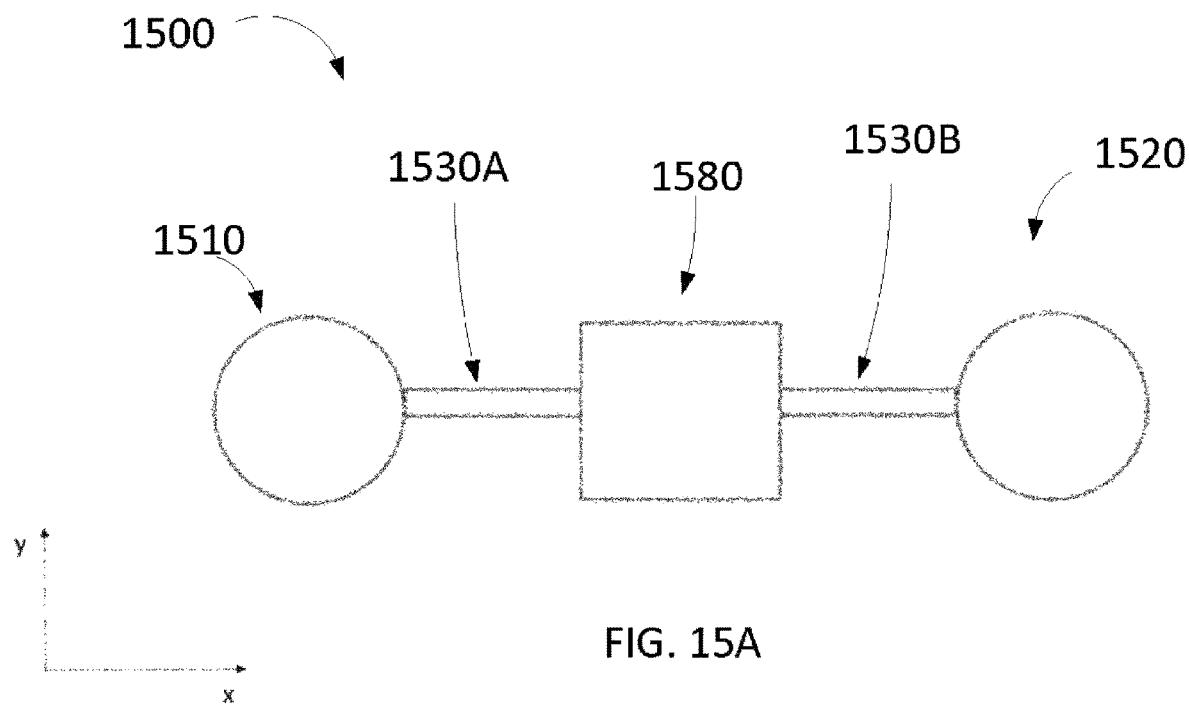
FIG. 15A is an illustration of a top view of a sensor system, according to an embodiment.
Figure 15B:
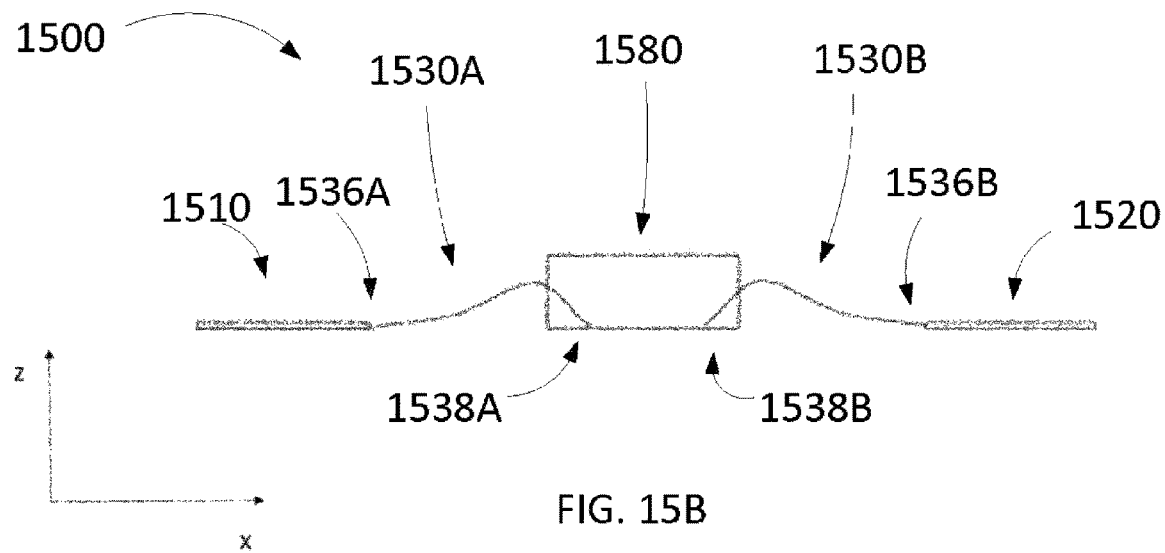
FIG. 15B is an illustration of a side view of the sensor system of FIG. 15A.

In some embodiments, a portion of each of a first connecting member and a second connecting member can be disposed within a housing of an assembly. For example, FIGS. 15A and 15B are schematic illustrations of a top view and a side view of a system 1500. The system 1500 includes a first assembly 1510, a second assembly 1520, and a third assembly 1580. The first assembly 1510 can be coupled to the third assembly 1580 via a first connecting member 1530A and the second assembly 1520 can be coupled to the third assembly 1580 via a second connecting member 1530B. The system 1500 can be similar in structure and/or function to any of the systems described herein. For example, the first assembly 1510 and the second assembly 1520 can be the same or similar in structure and/or function to any of the assemblies described herein, such as the first assembly 1410 and/or the second assembly 1420. The third assembly 1580 can be the same or similar in structure and/or function to any of the assemblies described herein, such as the third assembly 1480. The first connecting member 1530A and the second connecting member 1530B can each be the same or similar to any of the connecting members described herein, such as, for example, the first connecting member 1430A and the second connecting member 1430B.

The first connecting member 1530A has a first end 1536A coupled to the first assembly 1510 and a second end 1538A coupled to the third assembly 1580. The second connecting member 1530B has a first end 1536B coupled to the second assembly 1520 and a second end 1538B coupled to the third assembly 1580. As shown in FIG. 15B, the second end 1538A and the second end 1538B can be disposed within a housing of the third assembly 1580 such that a smaller portion of each of the first connecting member 1530A and the second connecting member 1530B is accessible from an exterior of the system 1500. For example, the third assembly 1580 can include an opening configured to receive a portion of the first connecting member 1530A, and the first connecting member 1530A can move within the opening as the first connecting member 1530A transitions between an initial configuration or shape and an expanded or contracted configuration or shape. Thus, an area or space bounded by a skin-facing surface of the first connecting member 1530A, an outer surface of the third assembly 1580, and a surface of the patient to which the system 1500 is coupled can be smaller than the space bounded by a skin-facing surface of the first connecting member 1430A and a surface of the patient to which the system 1400 is coupled when the first connecting member 1530A and the first connecting member 1430A are otherwise in the same configuration.

While shown in FIGS. 14B and 15B as having an arched or curved shape in the vertical direction (Y direction), in some embodiments the connecting members (1430A, 1430B, 1530A and 1530B) can include, contract and/or deform into any suitable shape. For example, in some embodiments the connecting members can have a serpentine shape, a sinusoidal shape, a zig-zag shape, a repeating sawtooth shape, a repeating triangle shape, and/or any combination of shapes lying in an X-Z plane (e.g., as viewed from a side view).

In some implementations, a system, such as any of the systems described herein, can include one or more connecting members having a combination of the features described with respect to the connecting members described herein. For example, a connecting member can have an overall horizontal width and a vertical height relative to a surface of the patient to which a system including the connecting member is attached that are both configured to change (e.g., contract or expand) as the connecting member deforms in response to skin deformation. For example, in a default or contracted configuration, the connecting member can, for example, have a serpentine shape, a sinusoidal shape, a zig-zag shape, a repeating sawtooth shape, a repeating triangle shape, and/or any combination of shapes lying in an X-Y plane (e.g., as viewed in a top view), and can have an arched or curved shape lying in an X-Z plane (e.g., as viewed from a side view).

In some implementations, the electrodes of any of the systems described herein (e.g., system 100) may be configured to detect conductive or inductive signals generated by an ingestible event marker of an ingestible pill disposed within a patient or conductive or inductive signals generated by any other ingestible or implantable device.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

In some embodiments, the systems (or any of its components) described herein can include a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Although various embodiments have been described as having particular features and/or combinations of components, other embodiments are possible having a combination of any features and/or components from any of the embodiments where appropriate.

In some embodiments, a system includes a first assembly, a second assembly, and a connecting member. The first assembly includes a first electrode and a first adhesive portion. The first assembly is configured to be coupled to a surface of a patient via the first adhesive portion. The second assembly includes a second electrode and a second adhesive portion. The second assembly is configured to be coupled to the surface of the patient via the second adhesive portion. The connecting member has a first end, a second end, and a third adhesive portion. The first end is coupled to the first assembly and the second end is coupled to the second assembly. The connecting member is configured to transition between a first configuration and a second configuration. A distance between the first end and the second end of the connecting member in the first configuration is a first distance. A distance between the first end and the second end of the connecting member in the second configuration is a second distance different from the first distance. The connecting member is configured to be coupled to the surface of the patient via the third adhesive portion in both the first configuration and the second configuration.

In some embodiments, the connecting member is configured to transition from the first configuration to the second configuration based at least in part on movement of the first assembly relative to the second assembly due to deformation of the surface of the patient.

In some embodiments, the connecting member is biased toward the first configuration.

In some embodiments, the connecting member is configured to be coupled to the surface of the patient via the third adhesive portion during the transition from the first configuration to the second configuration.

In some embodiments, the connecting member includes a skin-facing surface, the third adhesive portion configured to cover a portion of the skin-facing surface.

In some embodiments, the connecting member further includes a fourth adhesive portion. The third adhesive portion is disposed on a skin-facing surface of the connecting member at a first location. The fourth adhesive portion is disposed on a skin-facing surface of the connecting member at a second location.

In some embodiments, the connecting member includes a first segment, a second segment, and a third segment. The first segment is coupled to the second segment via a first flexible hinge. The second segment is coupled to the third segment via a second flexible hinge.

In some embodiments, the connecting member includes one or more conductive members configured to electrically couple the first assembly to the second assembly.

In some embodiments, the connecting member has a first sinusoidal shape having a first frequency in the first configuration and a second sinusoidal shape having a second frequency in the second configuration, the second frequency different from the first frequency.

In some embodiments, a system includes a first assembly, a second assembly, and a composite assembly. The first assembly includes a first electrode and a first housing. The first assembly is configured to be coupled to a surface of a patient's skin via a first adhesive portion. The second assembly includes a second electrode and a second housing. The second assembly is configured to be coupled to a surface of a patient's skin via a second adhesive portion. The composite assembly includes a processor and a composite board having a flexible portion. The flexible portion has a first end and a second end. The processor is disposed between the first electrode and the first housing. The composite assembly is configured to transition from a first configuration to a second configuration. A distance between the first end and the second end of the flexible portion in the first configuration being a first distance. A distance between the first end and the second end of the flexible portion in the second configuration being a second distance different from the first distance.

In some embodiments, the system includes a connecting member having a third housing and the flexible portion of the composite assembly is disposed within the third housing. The third housing, the first housing, and the second housing collectively form a cover layer and a bottom layer. The flexible composite assembly is disposed between the cover layer and the bottom layer.

In some embodiments, the composite assembly includes an energy storage device. The energy storage device is disposed within the second housing.

In some embodiments, a system includes a first assembly, a second assembly, and a composite assembly. The first assembly includes a first electrode and a first adhesive portion. The first assembly is configured to be coupled to a surface of a patient via the first adhesive portion. The second assembly includes a second electrode and a second adhesive portion. The second assembly configured to be coupled to a surface of a patient via the second adhesive portion. The composite assembly having a flexible portion, the flexible portion having a first end, a second end, and a plurality of layers. Each layer from the plurality of layers having a conductor extending between the first end and the second end. The first end is coupled to the first assembly and the second end is coupled to the second assembly. The composite assembly is configured to electrically couple the first assembly with the second assembly. The flexible portion is configured to transition from a first configuration to a second configuration. A distance between the first end and the second end of the flexible portion in the first configuration being a first distance. A distance between the first end and the second end of the flexible portion in the second configuration being a second distance different from the first distance. The flexible portion configured to be coupled to a surface of a patient via a third adhesive portion in both the first configuration and the second configuration.

In some embodiments, a conductor of a first layer of the plurality of layers is disposed a first distance away from a bottom surface of the flexible portion and a conductor of a second layer of the plurality of layers is disposed a second distance away from the bottom surface of the flexible portion.

In some embodiments, a first layer from the plurality of layers is stacked directly above a second layer from the plurality of layers.

In some embodiments, the composite assembly includes a printed circuit board.

The invention claimed is:

1. A system, comprising:
a first assembly including a first electrode and a first adhesive portion, the first assembly configured to be coupled to a surface of a patient via the first adhesive portion;
a second assembly including a second electrode and a second adhesive portion, the second assembly configured to be coupled to the surface of the patient via the second adhesive portion; and
a connecting member having a first end, a second end, and a third adhesive portion, the first end coupled to the first assembly and the second end coupled to the second assembly, the connecting member configured to transition between a first configuration and a second configuration, a distance between the first end and the second end of the connecting member in the first configuration being a first distance, a distance between the first end and the second end of the connecting member in the second configuration being a second distance different from the first distance, the connecting member configured to be coupled to the surface of the patient via the third adhesive portion in both the first configuration and the second configuration,
wherein the connecting member has a composite assembly portion, the composite assembly portion having an insulative portion and a plurality of conductive traces each exposed on an outer surface of an entire length of the composite assembly and electrically coupling the first and second assemblies, such that the insulative portion surrounds each of the conductive traces on all sides except for the outer surface;
wherein the plurality of conductive traces has a first conductive trace and a second conductive trace,
wherein the first conductive trace and the second conductive trace are disposed at varying locations relative to a skin-facing surface of the composite assembly portion, such that the first conductive trace is disposed farther from the skin-facing surface than the second conductive trace,
wherein the first conductive trace is vertically arranged relative to the second conductive trace such that the composite assembly portion is narrower than if the first conductive trace were horizontally arranged relative to the second conductive trace, and wherein a remaining portion of the connecting member not including the composite assembly portion does not include any of the plurality of conductive traces.

2. The system of claim 1, wherein the connecting member is configured to transition from the first configuration to the second configuration based at least in part on movement of the first assembly relative to the second assembly due to deformation of the surface of the patient.

3. The system of claim 1, wherein the connecting member is biased toward the first configuration.

4. The system of claim 1, wherein the connecting member is configured to be coupled to the surface of the patient via the third adhesive portion during the transition from the first configuration to the second configuration.

5. The system of claim 1, wherein the connecting member includes the skin-facing surface, the third adhesive portion configured to cover a portion of the skin-facing surface.

6. The system of claim 1, wherein the connecting member further includes a fourth adhesive portion, the third adhesive portion disposed on the skin-facing surface of the connecting member at a first location, the fourth adhesive portion disposed on the skin-facing surface of the connecting member at a second location.

7. The system of claim 1, wherein the connecting member includes a first segment, a second segment, and a third segment, the first segment coupled to the second segment via a first flexible hinge, the second segment coupled to the third segment via a second flexible hinge.

8. The system of claim 1, wherein the connecting member has a first sinusoidal shape having a first frequency in the first configuration and a second sinusoidal shape having a second frequency in the second configuration, the second frequency different from the first frequency.

9. The system of claim 1, wherein the plurality of conductive traces has a third conductive trace electrically coupling the first and second assemblies, the third conductive trace being disposed side by side with the second conductive trace.

10. The system of claim 1, wherein the plurality of conductive traces has a third conductive trace and a fourth conductive trace electrically coupling the first and second assemblies, the fourth conductive trace being disposed side by side with the second conductive trace while the third conductive trace being disposed farther from the skin-facing surface than the fourth conductive trace and side by side with the first conductive trace.

11. The system of claim 10, wherein the third conductive trace is vertically arranged relative to the fourth conductive trace such that the composite assembly portion can be narrower than if at least one of the first conductive trace or the third conductive trace were horizontally arranged relative to the second conductive trace and the fourth conductive trace.

12. The system of claim 1, wherein the plurality of conductive traces has a third conductive trace and a fourth conductive trace electrically coupling the first and second assemblies, the third conductive trace and the fourth conductive trace being vertically arrange relative to both the first conductive trace and the second conductive trace such that the composite assembly portion can be narrower than if at least one of the third conductive trace or the fourth conductive trace were horizontally arranged relative to the first conductive trace or the second conductive trace.

13. The system of claim 1, wherein the plurality of conductive traces has a third conductive trace electrically coupling the first and second assemblies, the third conductive trace being disposed side by side with the first conductive trace.

14. The system of claim 1, wherein the plurality of conductive traces are exposed on the outer surface by each being etched into or printed on the outer surface of the entire length of the composite assembly.

* * * * *

UNITED STATES PATENT AND TRADEMARK OFFICE
CERTIFICATE OF CORRECTION

| | |
|---|---|
| PATENT NO. | : 12,383,181 B2 |
| APPLICATION NO. | : 17/424757 |
| DATED | : August 12, 2025 |
| INVENTOR(S) | : Tomi Mattila et al. |

It is certified that error appears in the above-identified patent and that said Letters Patent is hereby corrected as shown below:

On the Title Page

Item [73], replace "OTSUKA PHARMACEUTICAL CO, LTD."
With --OTSUKA PHARMACEUTICAL CO., LTD.--

Signed and Sealed this
Second Day of September, 2025

Coke Morgan Stewart
*Acting Director of the United States Patent and Trademark Office*